(12) United States Patent
Chen

(10) Patent No.: US 7,566,787 B2
(45) Date of Patent: Jul. 28, 2009

(54) SMALL MOLECULE CYCLIN D1 ABLATIVE AGENTS

(75) Inventor: Ching-Shih Chen, Upper Arlington, OH (US)

(73) Assignee: The Ohio State University, Columbus, OH (US)

(*) Notice: Subject to any disclaimer, the term of this patent is extended or adjusted under 35 U.S.C. 154(b) by 72 days.

(21) Appl. No.: 11/315,569

(22) Filed: Dec. 22, 2005

(65) Prior Publication Data

US 2006/0252802 A1  Nov. 9, 2006

Related U.S. Application Data

(60) Provisional application No. 60/638,522, filed on Dec. 22, 2004.

(51) Int. Cl.
  *C07D 277/00* (2006.01)
  *C07D 319/14* (2006.01)
  *C07D 417/00* (2006.01)

(52) U.S. Cl. .................. 548/200; 548/146; 546/269.7; 549/356; 549/358; 549/362

(58) Field of Classification Search ............... 548/200, 548/146; 549/359, 358, 362; 546/269.7
See application file for complete search history.

(56) References Cited

U.S. PATENT DOCUMENTS 5,801,173 A * 9/1998 Lohray et al. ............ 514/253.1

FOREIGN PATENT DOCUMENTS

JP  0 454 501 A2 * 4/1991 ................ 514/253

OTHER PUBLICATIONS

Kwon, Younggil. Handbook of Essential Pharmacokinetics, Pharmacodynamics and Drug Metabolism for Industrial Scientists. Jun. 24, 2001. Apr. 24, 2008.*
Metabolomics [online], Retrieved from the Internet Apr. 24, 2008, www.en.wikipedia.org/wiki/Metabolomics.*
Cancer Topics [online], Retrieved from the Internet Apr. 24, 2008, www.nci.gov/cancertopics/druginfo/alphalist/print?page=&keyword.*
Qin, Chunhua, et al., "Peroxisome Proliferator-activated Receptor y Agonists Induce Proteasome-dependent Degradation of Cyclin D1 and Estrogen Receptor a in MCF-7 Breast Cancer Cells", Cancer Research 63, 958-964, Mar. 1, 2003.
Palakurthia, Sangeetha S., "Anticancer Effects of Thiazolidinediones are Independent of Peroxisome Proliferator-activated Receptor y and Mediated by Inhibition of Translation Initiation", Cancer Research 61, 6213-6218, Aug. 15, 2001.

* cited by examiner

*Primary Examiner*—Kamal A Saeed
*Assistant Examiner*—Samantha L Shterengarts
(74) *Attorney, Agent, or Firm*—Calfee, Halter & Griswold LLP

(57) ABSTRACT

Cyclin D1 ablative agents and methods of using these agents in the treatment of cancers, and particularly breast cancer. Also provided are methods of treating cancer, the method comprising administering a therapeutically effective amount of one of the cyclin D1 ablative agents described herein to a subject in need of such treatment. Also provided are methods of treating cancers comprising using the cyclin D1 ablative agents described herein in combination therapies with existing chemotherapeutic agents.

21 Claims, 8 Drawing Sheets

SMALL MOLECULE CYCLIN D1 ABLATIVE AGENTS

CROSS-REFERENCE TO RELATED APPLICATIONS

This application claims priority to US Provisional Patent Application No. 60/638,522, filed Dec. 22, 2004, the entirety of which is incorporated herein by reference.

STATEMENT REGARDING FEDERALLY FUNDED RESEARCH

This invention was funded, at least in part, by grant CA-94829 from the National Cancer Institute and grant DAMD17-02-1-0117. The federal government may have certain rights in this invention.

BACKGROUND OF THE INVENTION

Cyclin D1 represents an important downstream effector of diverse proliferative and transforming signaling pathways, including those mediated by β-catenin (Shtutman et al., 1999), ERα (Lukas et al., 1996; Prall et al., 1998; Wilcken et al., 1997), Her-2/Neu (Lee et al., 2000), NFκB (Henry et al., 2000; Joyce et al., 1999), Rac (Westwick et al., 1997), Ras (Albanese et al., 1995), Src (Lee et al., 1999), STATs (Bromberg et al., 1999; Matsumura et al., 1999), and Wnt (D'Amico et al., 2000). In mammary cells, transcriptional activation of cyclin D1 in response to these mitogenic signals leads to G1/S progression and increased proliferation. Cyclin D1 overexpression has been implicated in oncogene-induced mammary tumorigenesis as it is noted in over 50% of primary breast carcinomas correlating with poor prognosis (Kenny et al., 1999; McIntosh et al., 1995). In addition to activating cyclin-dependent kinases (CDKs) and sequestering of CDK inhibitors in the G1/S transition, the function of cyclin D1 as a CDK-independent activator of estrogen receptor α (ERα) is especially noteworthy (Lamb et al., 2000; McMahon et al., 1999; Neuman et al., 1997; Zwijsen et al., 1997). Cyclin D1 overexpression confers resistance to antiestrogens in breast cancer cells (Hui et al., 2002; Musgrove et al., 2001), and represents a negative predictive factor for tamoxifen response (Stendahl et al., 2004). Together, these findings suggest that an anti-cyclin D1 therapy might be highly specific for treating human breast cancer (Yu et al., 2001).

Accordingly, a need exists for new cyclin D1 ablative agents useful in the treatment of cancers, particularly breast cancers.

SUMMARY OF THE INVENTION

Provided are cyclin D1 ablative agents and methods of using these agents in the treatment of cancers, and particularly breast cancer. Also provided are methods of treating cancer, the method comprising administering a therapeutically effective amount of one of the cyclin D1 ablative agents described herein to a subject in need of such treatment. In one embodiment, the cancer is breast cancer, and the subject is a human subject. Also provided are methods of treating cancers comprising using the cyclin D1 ablative agents described herein in combination therapies with existing chemotherapeutic agents.

DETAILED DESCRIPTION OF THE INVENTION

Figure 1:
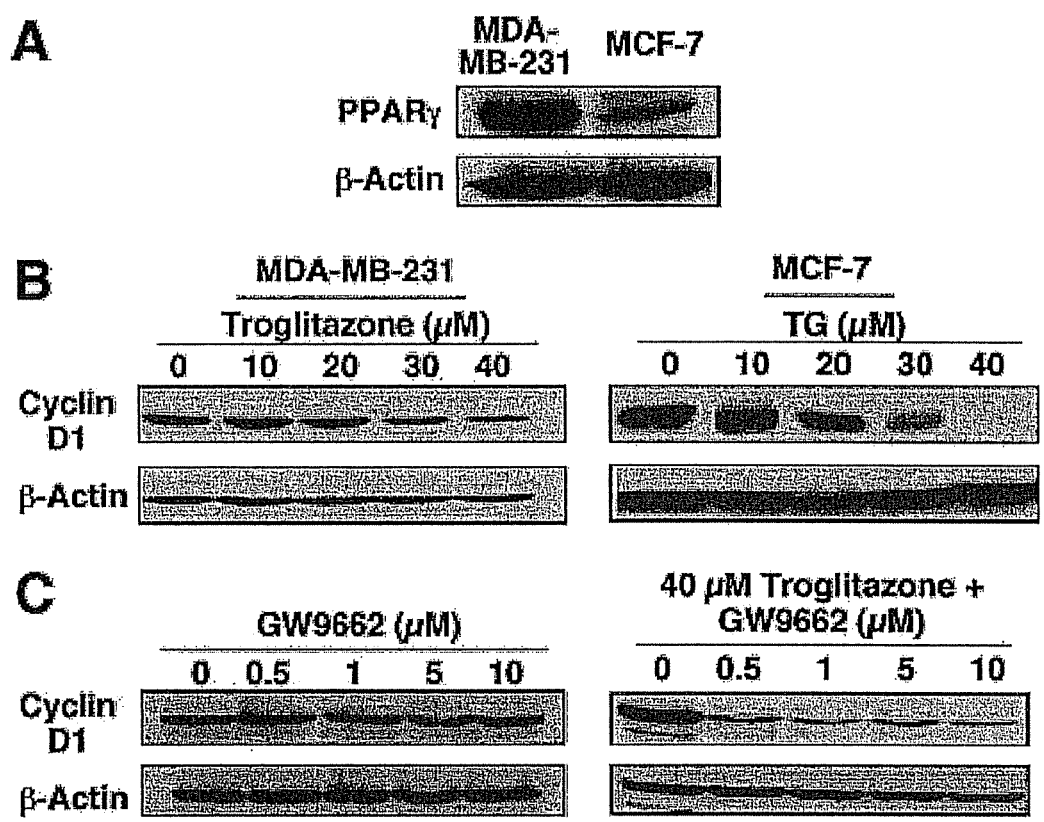
FIG. 1. Effect of TG on cyclin D1 down-regulation in breast cancer cells is irrespective of PPARγ expression levels. A, differential expression levels of PPARγ in MDA-MB-231 and MCF-7 cells. B, dose-dependent effect of TG on cyclin D1 repression in MDA-MB-231 and MCF-7 cells. Cells were treated with TG at the indicated concentrations in 5% FBS-supplemented DMEM-F12 medium for 24 h. These Western blots are representative of three independent experiments. C, High doses of the PPARγ antagonist GW9662 have no effect on cyclin D1 expression (left panel) or TG-mediated cyclin D1 ablation (right panel) in MCF-7 cells.

Provided are new cyclin D1 ablative agents useful in treating unwanted proliferating cells, including, but not limited to cancers and precancers. Some specific embodiments of the cyclin D1 ablative agents are shown in Table 1, below. The D1 ablative agents described herein further include derivatives, pharmacuetically acceptable salts, and metabolites thereof. Also provided are methods of using the cyclin D1 ablative agents described herein in the treatment of unwanted proliferating cells in a subject, the method comprising administering a therapeutically effective amount of a cyclin D1 ablative agent described herein to a subject in need of such treatment. In one embodiment, the method is a method of treating cancer in a subject comprising the step of administering a therapeutically effective amount of a cyclin D1 ablative agent described herein to a subject having cancer. In one embodiment, the method comprises a method of treating breast cancer in a subject comprising the step of administering a therapeutically effective amount of a cyclic D1 ablative agent described herein to a subject having breast cancer. Also provided are methods of preventing the proliferation of unwanted proliferating cells in a subject, the method comprising the step of administering a therapeutically effective amount of a cyclin D1 ablative agent described herein to a subject at risk of developing a condition characterized by unwanted proliferation cells. In one embodiment, the method is a method of preventing cancer. In another embodiment, the method is a method of preventing breast cancer. In some embodiments, the methods treating unwanted proliferating cells, including cancers and precancers, comprise inducing apoptosis in the unwanted proliferating cells by administering an effective amount of the cyclin D1 ablative agent to the subject in need of such treatment.

In one embodiment the cyclin D1 ablative agents described herein have the following structure:

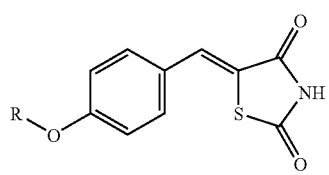

I wherein R is selected from aryl, heteroaryl, cycloalkyl, heterocycloalkyl, alkylaryl, and combinations thereof; and wherein R may be substituted at one or more substitutable positions with a hydroxyl, or alkyl substituent. In some embodiments, R is selected from the group consisting of

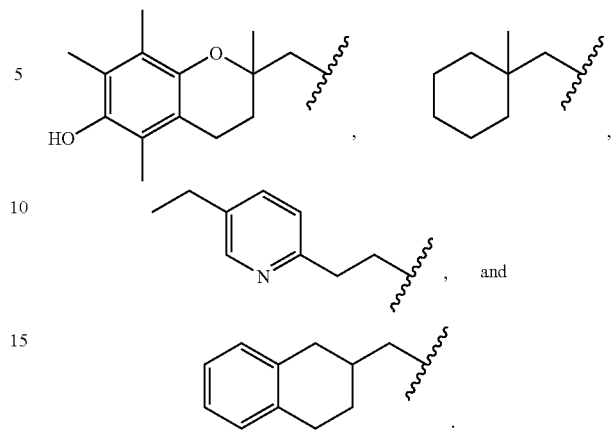

, and

Some embodiments include:

TABLE 1

| Entry | compound | R | IC50 for MTT | IC50 for WB |
|---|---|---|---|---|
| 1 | Δ2-TG | | 57 | 22 |
| 2 | Δ2-CG | | 70 | 13 |
| 3 | Δ2-PG | | | |
| 4 | TG-15 | | 37 | 3.8 |

In another embodiment, the cyclin D1 ablative agents described herein have the following structure:

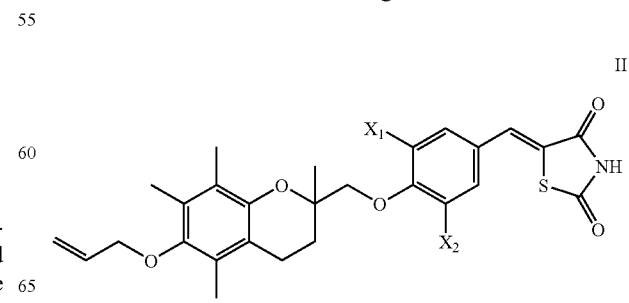

II wherein $X_1$ is selected from the group consisting of H, alkyl, alkoxy, halo, nitro, and combinations thereof; and $X_2$ is selected from the group consisting of H, alkyl, alkoxy, halo, and combinations thereof. In some embodiments, $X_1$ is selected from H, Br, $CH_3$, $OCH_3$, $OCH_2CH_3$, $NO_2$, and Cl; and $X_2$ is selected from H, $CH_3$, $OCH_3$, and Br. Some embodiments include:

TABLE 2

| Entry | compound | X1 | X2 | IC50 for MTT | IC50 for WB |
|---|---|---|---|---|---|
| 5 | TG-6 | H | H | 9 | 3 |
| 6 | TG-27 | Br | H | 28 | >7.5 |
| 7 | TG-28 | OMe | H | 14.5 | 2.3 |
| 8 | TG-29 | Me | H | 23.5 | 3.6 |
| 9 | TG-52 | Me | Me | 10.5 | 7.5 |
| 10 | TG-54 | Br | OMe | 17.5 | 3.8 |
| 11 | TG-55 | OEt | H | 17 | >7.5 |
| 12 | | Br | Br | | |
| 13 | | NO2 | H | | |
| 14 | | Cl | H | | |

In another embodiment, the cyclin D1 ablative agents described herein have the following structure:

III

wherein $X_1$ is selected from the group consisting of H, alkyl, alkoxy, halo, nitro, haloalkylaryl, haloaryl, alkylaryl, and combinations thereof.; and $X_2$ is selected from the group consisting of H, alkyl, alkoxy, halo, and combinations thereof. In some embodiments, $X_1$ is selected from the group consisting of H, methyl, methoxy, ethoxy, fluoro, chloro, bromo, nitro, trifluoromethylphenyl, fluorophenyl, and ethylphenyl; and $X_2$ is selected from the group consisting of H, methyl, methoxy, and bromo. Some embodiments are shown in the table below.

TABLE 3

| Entry | compound | X1 | X2 | IC50 for MTT | IC50 for WB |
|---|---|---|---|---|---|
| 15 | TG-14 | H | H | 14.5 | 7 |
| 16 | TG-16 | OMe | H | 15 | 5.6 |
| 17 | TG-17 | Me | H | 14.5 | 3.2 |
| 18 | TG-30 | F | H | 12.5 | 7.2 |
| 19 | TG-31 | 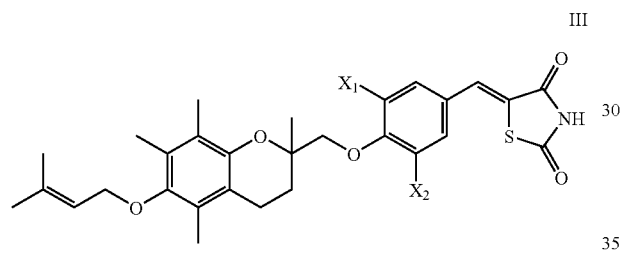—CF3 | H | >50 | >7.5 |
| 20 | TG-32 | —F (aryl) | H | 19.5 | >7.5 |

TABLE 3-continued

| Entry | compound | X1 | X2 | IC50 for MTT | IC50 for WB |
|---|---|---|---|---|---|
| 21 | TG-33 | 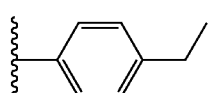 | H | >50 | >7.5 |
| 22 | TG-34 | Br | Br | 15.5 | 2.7 |
| 23 | TG-35 | N2O | H | 38 | 2.7 |
| 24 | TG-44 | Br | OMe | 14.5 | >7.5 |
| 25 | TG-45 | OEt | H | 13 | 6.7 |
| 26 | TG-88 | Br | H | 14.5 | >7.5 |
| 27 | | Me | Me | | |
| 28 | | Cl | H | | |

In another embodiment, the cyclin D1 ablative agents described herein have the following structure:

IV

wherein $X_1$ is selected from the group consisting of H, halo, and combinations thereof and Y is selected from the group consisting of alkylaryl, alkenylaryl, alkenyl, ester carboxylic acids, ester alcohols, and combinations thereof. In some embodiments, $X_1$ is selected from the group consisting of H and Br, and Y is selected from the group consisting of

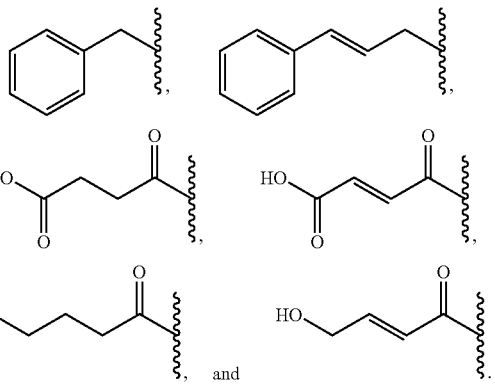

Some embodiments are shown in the table below.

TABLE 4

| Entry | compound | X1 | Y | IC50 for MTT | IC50 for WB |
|---|---|---|---|---|---|
| 29 | TG-10 | H | cinnamyl | 19 | >7.5 |
| 30 | TG-11 | Br | cinnamyl | 28.5 | >7.5 |
| 31 | TG-12 | H | benzyl | 16.67 | 3.6 |
| 32 | TG-13 | H | HOOC-CH2CH2-C(O)-CH2- | >50 | >7.5 |
| 33 | | Br | HOOC-CH2CH2-C(O)-CH2- | | |
| 34 | | H | HOOC-CH=CH-C(O)-CH2- | | |
| 35 | | Br | HOOC-CH=CH-C(O)-CH2- | | |
| 36 | | H | HO-CH2CH2CH2-C(O)-CH2- | | |
| 37 | | Br | HO-CH2CH2CH2-C(O)-CH2- | | |
| 38 | | Br | HO-CH2-CH=CH-C(O)-CH2- | | |

In another embodiment, the cyclin D1 ablative agents described herein have the following structure:

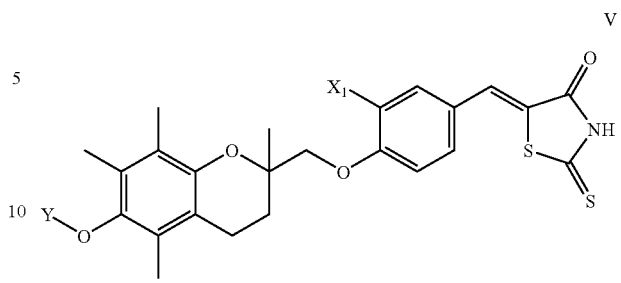

wherein $X_1$ is selected from the group consisting of H, halo, and combinations thereof; and Y is selected from the group consisting of straight-chain alkenyl, branched alkenyl, and combinations thereof. Some specific embodiments include:

TABLE 5

| Entry | compound | X1 | Y | IC50 for MTT | IC50 for WB |
|---|---|---|---|---|---|
| 39 | TG-3 | H | allyl | 11 | 3.5 |
| 40 | TG-89 | Br | prenyl | | |

In another embodiment, the cyclin D1 ablative agents described herein have the following structure:

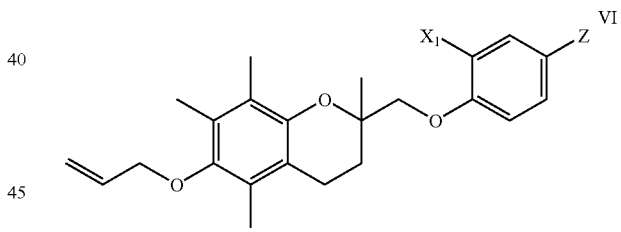

wherein $X_1$ is selected from the group consisting of H, alkoxy, halo, and combinations thereof; and Z is selected from the group consisting of

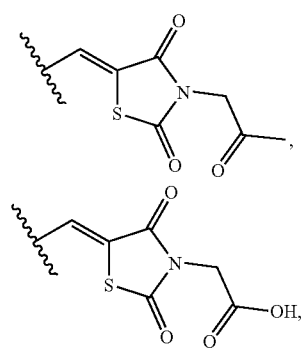

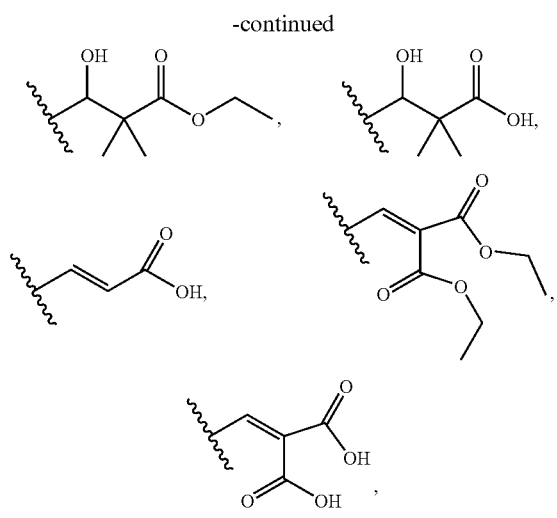

and combinations thereof. Some specific embodiments include:

TABLE 6

| Entry | compound | X1 | Z | IC50 for MTT | IC50 for WB |
|---|---|---|---|---|---|
| 41 | TG-9 | H | (thiazolidinedione-CH2COCH3) | >50 | >7.5 |
| 42 | | H | (thiazolidinedione-CH2COOH) | | |
| 43 | | OMe | (thiazolidinedione-CH2COOH) | | |
| 44 | | OEt | (thiazolidinedione-CH2COOH) | | |
| 45 | | H | (CH(OH)C(CH3)2COOEt) | | |

TABLE 6-continued

| Entry | compound | X1 | Z | IC50 for MTT | IC50 for WB |
|---|---|---|---|---|---|
| 46 | | OMe | (CH(OH)C(CH3)2COOEt) | | |
| 47 | | OEt | (CH(OH)C(CH3)2COOEt) | | |
| 48 | | H | (CH(OH)C(CH3)2COOH) | | |
| 49 | | OMe | (CH(OH)C(CH3)2COOH) | | |
| 50 | | OEt | (CH(OH)C(CH3)2COOH) | | |
| 51 | | H | (CH=CHCOOH) | | |
| 52 | | OMe | (CH=CHCOOH) | | |
| 53 | | OEt | (CH=CHCOOH) | | |
| 54 | | H | (CH=C(COOEt)2) | | |
| 55 | | OMe | (CH=C(COOEt)2) | | |

TABLE 6-continued

| Entry | compound | X1 | Z | IC50 for MTT | IC50 for WB |
|---|---|---|---|---|---|
| 56 | | OEt | (diethyl malonate-ylidene) | | |
| 57 | | H | (malonic acid-ylidene) | | |
| 58 | | OMe | (malonic acid-ylidene) | | |
| 59 | | OEt | (malonic acid-ylidene) | | |

In another embodiment, the cyclin D1 ablative agents described herein have the following structure:

VII

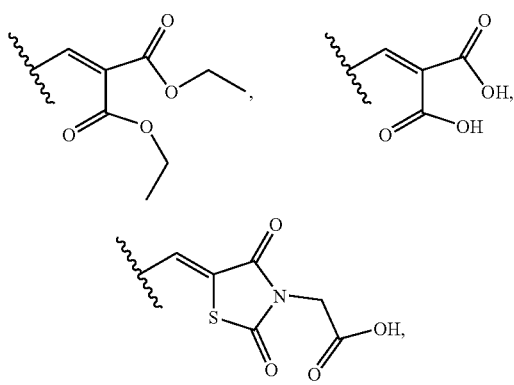

wherein $X_1$ is selected from the group consisting of H, halo, and combinations thereof and Z is selected from the group consisting of

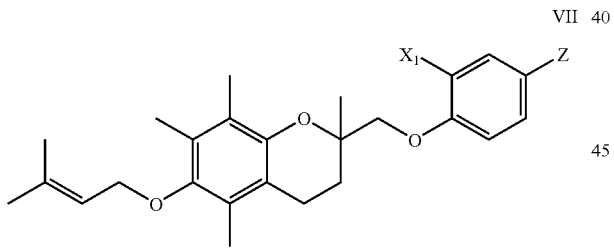

and combinations thereof. Some specific embodiments are shown in the table, below:

TABLE 7

| Entry | compound | X1 | Z | IC50 for MTT | IC50 for WB |
|---|---|---|---|---|---|
| 60 | TG-36 | Br | (dicyanomethylene) | >50 | >7.5 |
| 61 | TG-37 | Br | (acrylic acid) | 34 | >7.5 |
| 62 | TG-38 | Br | (3-hydroxy-2,2-dimethyl ethyl ester) | >50 | 4.5 |
| 63 | TG-39 | Br | (3-hydroxy-2,2-dimethyl acid) | 46 | >7.5 |
| 64 | TG-41 | Br | (diethyl malonate-ylidene) | >50 | >7.5 |
| 65 | TG-42 | Br | (malonic acid-ylidene) | >50 | >7.5 |

TABLE 7-continued

| Entry | compound | X1 | Z | IC50 for MTT | IC50 for WB |
|---|---|---|---|---|---|
| 66 | | H | 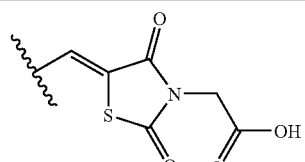 | | |
| 67 | | Br | 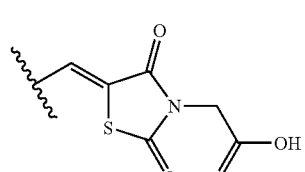 | | |
| 68 | | Cl | 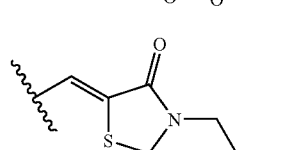 | | |

In another embodiment, the cyclin D1 ablative agents described herein have the following structure:

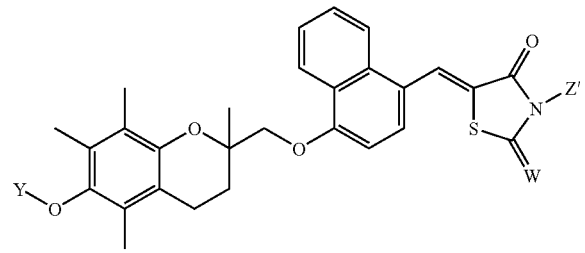

VIII wherein W is selected from O, S and combinations thereof; Y is selected from straight chain alkenyl, branched alkenyl and combinations thereof, and Z' is selected from H and carboxylic acid. Some specific embodiments are shown in the table below:

TABLE 8

| Entry | compound | W | Y | Z' | IC50 for MTT | IC50 for WB |
|---|---|---|---|---|---|---|
| 69 | TG-43 | O | 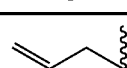 | H | 14.5 | 7.2 |
| 70 | TG-46 | S | 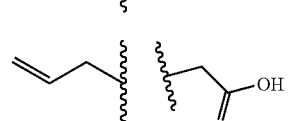 | H | 37.33 | 6.7 |

TABLE 8-continued

| Entry | compound | W | Y | Z' | IC50 for MTT | IC50 for WB |
|---|---|---|---|---|---|---|
| 71 | TG-53 | O |  | H | 14.5 | 3.4 |
| 72 | | O |  | | | |

In another embodiment, the cyclin D1 ablative agents described herein have the following structure:

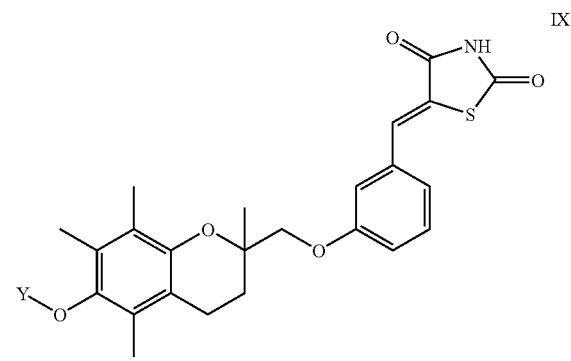

IX wherein Y is selected from straight chain alkenyl, branched alkenyl and combinations thereof. Some specific embodiments are shown in the table below:

TABLE 9

| Entry | compound | Y | IC50 for MTT | IC50 for WB |
|---|---|---|---|---|
| 73 | TG-51 | | 40 | 4.4 |
| 74 | | | | |

In another embodiment, the cyclin D1 ablative agents described herein have the following structure:

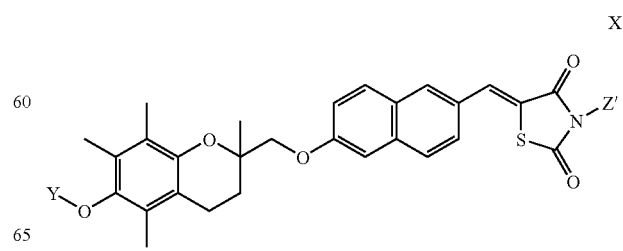

X wherein Y is selected from straight chain alkenyl, branched alkenyl and combinations thereof, and Z' is selected from H and carboxylic acid. Some specific embodiments are shown in the table below:

TABLE 10

| Entry | Y | Z' |
|---|---|---|
| 75 | CH₂=CHCH₂CH₂– | H |
| 76 | CH₂=CHCH₂CH₂– | –CH₂C(O)OH |
| 77 | (CH₃)₂C=CHCH₂– | H |

In another embodiment, the cyclin D1 ablative agents described herein have the following structure:

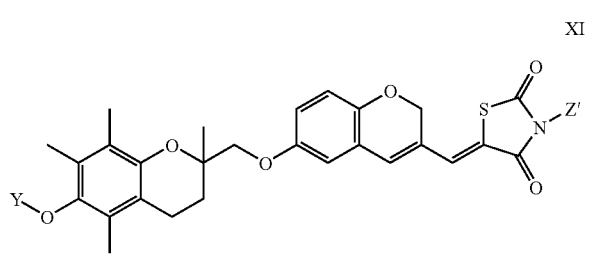

XI wherein Y is selected from straight chain alkenyl, branched alkenyl and combinations thereof, and Z' is selected from H and carboxylic acid. Some specific embodiments are shown in the table below:

TABLE 11

| Entry | Y | Z' |
|---|---|---|
| 78 | CH₂=CHCH₂CH₂– | H |
| 79 | CH₂=CHCH₂CH₂– | –CH₂C(O)OH |
| 80 | (CH₃)₂C=CHCH₂– | H |

As used herein, the term "prevention" includes either preventing the onset of a clinically evident unwanted cell proliferation altogether or preventing the onset of a preclinically evident stage of unwanted rapid cell proliferation in individuals at risk. Also intended to be encompassed by this definition is the prevention of metastasis of malignant cells or to arrest or reverse the progression of malignant cells. This includes prophylactic treatment of those at risk of developing precancers and cancers.

The terms "therapeutically effective" and "pharmacologically effective" are intended to qualify the amount of each agent which will achieve the goal of improvement in disease severity and the frequency of incidence over treatment of each agent by itself, while avoiding adverse side effects typically associated with alternative therapies.

The term "subject" for purposes of treatment includes any human or animal subject who has a disorder characterized by unwanted, rapid cell proliferation. Such disorders include, but are not limited to cancers and precancers. For methods of prevention the subject is any human or animal subject, and preferably is a human subject who is at risk of obtaining a disorder characterized by unwanted, rapid cell proliferation, such as cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs. In most embodiments, subject means a human.

The phrase "pharmaceutically acceptable salts" connotes salts commonly used to form alkali metal salts and to form addition salts of free acids or free bases. The nature of the salt is not critical, provided that it is pharmaceutically acceptable. Suitable pharmaceutically acceptable acid addition salts of compounds of formulae I and II may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, galactaric, and galacturonic acids. Suitable pharmaceutically acceptable base addition salts of the compounds described herein include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the compounds described herein. All of these salts may be prepared by conventional means from the corresponding compounds described herein by reacting, for example, the appropriate acid or base with the compound.

Where the term alkyl is used, either alone or with other terms, such as haloalkyl or alkylaryl, it includes $C_1$ to $C_{10}$ linear or branched alkyl radicals, examples include methyl, ethyl, propyl, isopropyl, butyl, tert-butyl, and so forth. The term "haloalkyl" includes $C_1$ to $C_{10}$ linear or branched alkyl radicals substituted with one or more halo radicals. Some examples of haloalkyl radicals include trifluoromethyl, 1,2-dichloroethyl, 3-bromopropyl, and so forth. The term "halo" includes radicals selected from F, Cl, Br, and I. Alkyl radical substituents of the present invention may also be substituted with other groups such as azido, for example, azidomethyl, 2-azidoethyl, 3-azidopropyl and so on.

The term aryl, used alone or in combination with other terms such as alkylaryl, haloaryl, or haloalkylaryl, includes such aromatic radicals as phenyl, biphenyl, and benzyl, as well as fused aryl radicals such as naphthyl, anthryl, phenanthrenyl, fluorenyl, and indenyl and so forth. The term "aryl" also encompasses "heteroaryls," which are aryls that have carbon and one or more heteroatoms, such as O, N, or S in the aromatic ring. Examples of heteroaryls include indolyl, pyrrolyl, and so on. "Alkylaryl" or "arylalkyl" refers to alkyl-substituted aryl groups such as butylphenyl, propylphenyl, ethylphenyl, methylphenyl, 3,5-dimethylphenyl, tert-butylphenyl and so forth. "Haloaryl" refers to aryl radicals in which one or more substitutable positions has been substituted with a halo radical, examples include fluorophenyl, 4-chlorophenyl, 2,5-chlorophenyl and so forth. "Haloalkylaryl" refers to aryl radicals that have a haloalkyl substituent.

Provided are pharmaceutical compositions for ablating cyclin D1 in MCF-7 cells specifically. These compounds are also useful for treating, preventing, or delaying the onset of a cancer in a subject in need of such treatment. The pharmaceutical composition comprises a therapeutically effective amount of a compound disclosed herein, or a derivative or pharmaceutically acceptable salt thereof, in association with at least one pharmaceutically acceptable carrier, adjuvant, or diluent (collectively referred to herein as "carrier materials") and, if desired, other active ingredients. The active compounds of the present invention may be administered by any suitable route known to those skilled in the art, preferably in the form of a pharmaceutical composition adapted to such a route, and in a dose effective for the treatment intended. The active compounds and composition may, for example, be administered orally, intra-vascularly, intraperitoneally, intra-nasal, intrabronchial, subcutaneously, intramuscularly or topically (including aerosol). With some subjects local administration, rather than system administration, may be preferred. Formulation in a lipid vehicle may be used to enhance bioavailability.

The administration of the present invention may be for either prevention or treatment purposes. The methods and compositions used herein may be used alone or in conjunction with additional therapies known to those skilled in the art in the prevention or treatment of disorders characterized by unwanted, rapid proliferation of cells. Alternatively, the methods and compositions described herein may be used as adjunct therapy. By way of example, the compounds of the present invention may be administered alone or in conjunction with other antineoplastic agents or other growth inhibiting agents or other drugs or nutrients, as in an adjunct therapy.

The phrase "adjunct therapy" or "combination therapy" in defining use of a compound described herein and one or more other pharmaceutical agents, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

For the purposes of combination therapy, there are large numbers of antineoplastic agents available in commercial use, in clinical evaluation and in pre-clinical development, which could be selected for treatment of cancers or other disorders characterized by rapid proliferation of cells by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallomatrix proteases inhibitors (MMP), such as MMP-13 inhibitors, or $\alpha_v\beta_3$ inhibitors may be used. Suitable agents which may be used in combination therapy will be recognized by those of skill in the art. Similarly, when combination therapy is desired, radioprotective agents known to those of skill in the art may also be used.

When preparing the compounds described herein for oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

For treating cancers or other unwanted proliferative cells that are localized in the G.I. tract, the compound may be formulated with acid-stable, base-labile coatings known in the art which begin to dissolve in the high pH small intestine. Formulation to enhance local pharmacologic effects and reduce systemic uptake are preferred.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, and the particular compound employed, the location of the unwanted proliferating cells, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

Abbreviations: CDK, cyclin-dependent kinase; ERα, estrogen receptor α; PPARγ, peroxisome proliferator-activated receptor γ; $PGJ_2$, 15-deoxy-Δ12,14-prostaglandin $J_2$; TZD, thiazolidenedione; TG, troglitazone; CG, ciglitazone; RG, rosiglitazone; PG, pioglitazone; Δ2-TG, 5-[4-(6-hydroxy-2,5,7,8-tetramethyl-chroman-2-yl-methoxy)-benzylidene]-2,4-thiazolidinedione; Δ2-CG, 5-[4-(1-methyl-cyclohexylmethoxy)-benzylidene]-thiazolidine-2,4-dione; Δ2-TG-6, 5-[4-(6-allyoxy-2,5,7,8-tetramethyl-chroman-2-yl-methoxy)-benzylidene]-2,4-thiazolidinedione; FBS, fetal bovine serum; MTT, 3-(4,5-dimethylthiazol-2-yl)-2,5-diphenyl-2H-tetrazolium bromide.

Table 12 shows several embodiments of the cyclin D1 ablative agents described herein. Tables 2, 3 and 4 show $IC_{50}$ values for several cylcin D1 ablative agents (western blot data and cell viability data) in MCF-7 cells.

TABLE 12

| Entry | compound | structure |
|---|---|---|
| 1 | Δ2-TG | 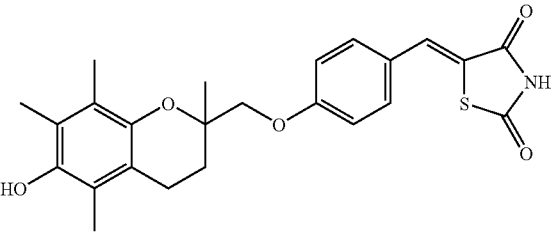 |
| 2 | Δ2-CG | 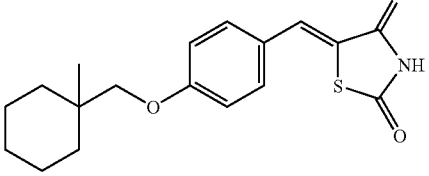 |
| 3 | Δ2-PG | 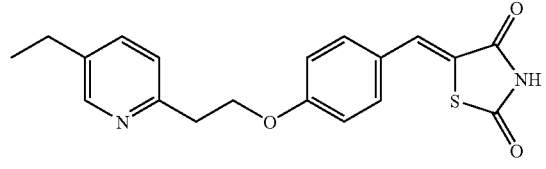 |
| 4 | TG-6 | 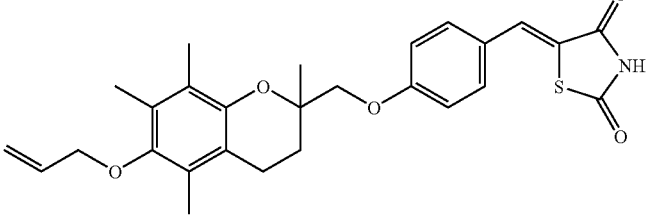 |
| 5 | TG-3 | 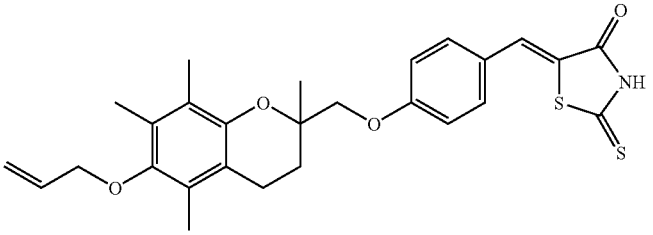 |

TABLE 12-continued

| Entry | compound | structure |
|---|---|---|
| 6 | TG-9 | 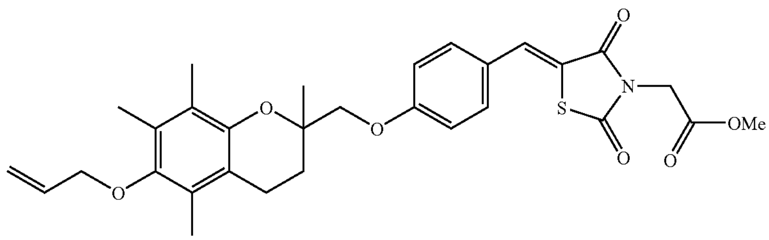 |
| 7 | TG-10 | 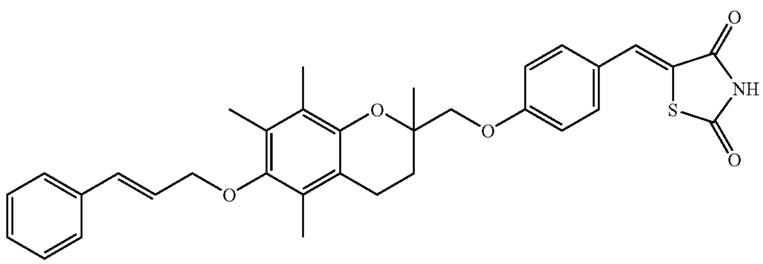 |
| 8 | TG-11 | 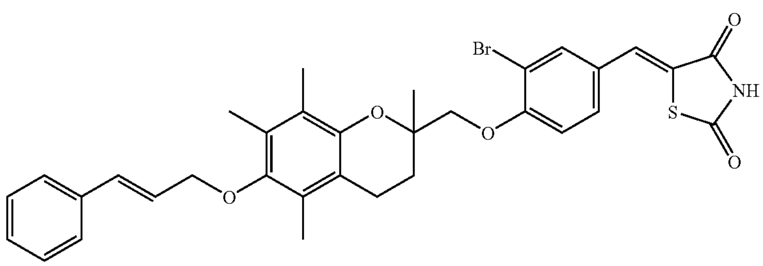 |
| 9 | TG-12 | 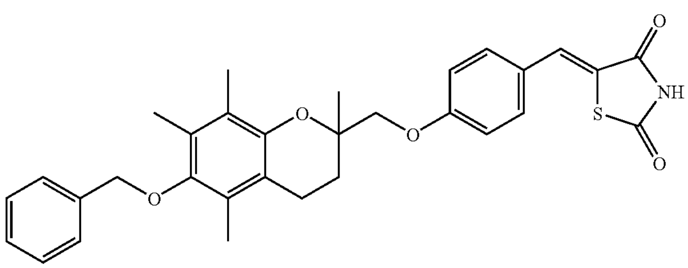 |
| 10 | TG-13 | 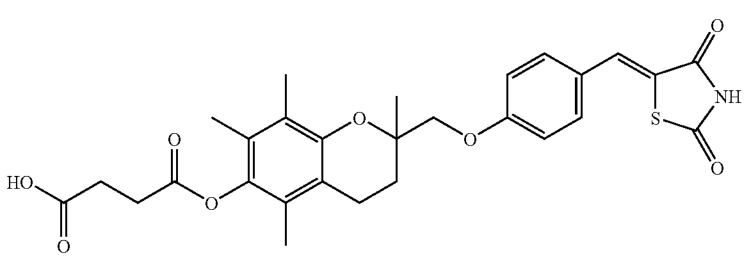 |
| 11 | TG-14 | 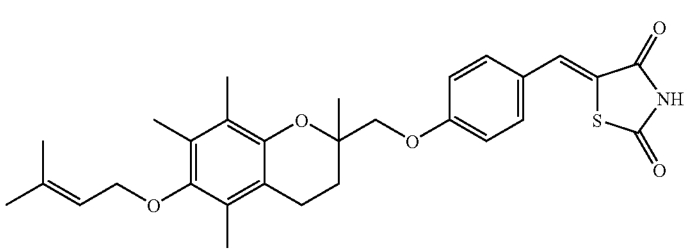 |

TABLE 12-continued

| Entry | compound | structure |
|---|---|---|
| 12 | TG-15 | 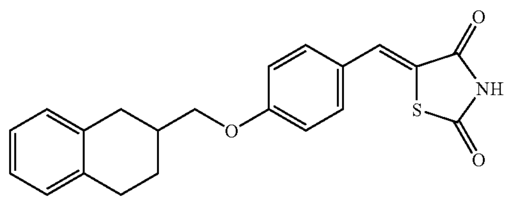 |
| 13 | TG-16 | 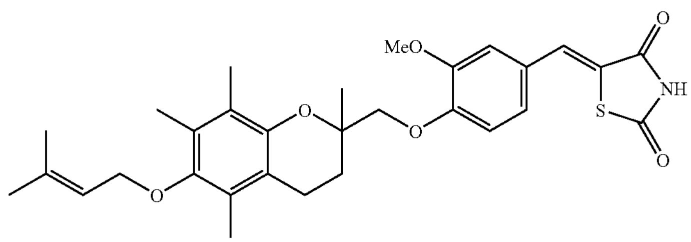 |
| 14 | TG-17 | 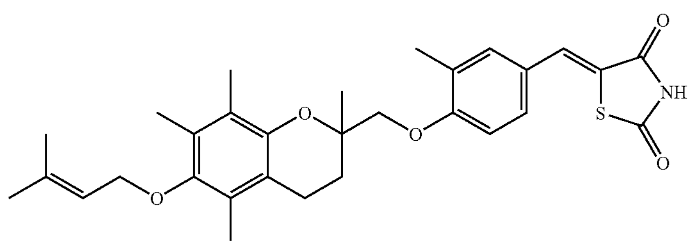 |
| 15 | TG-27 | 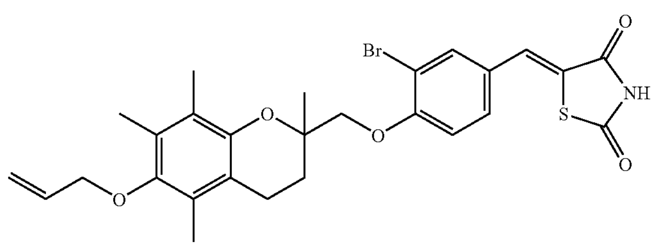 |
| 16 | TG-28 | 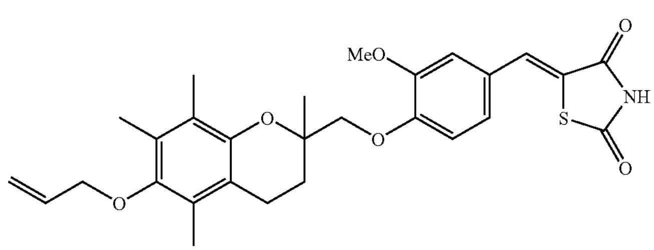 |
| 17 | TG-29 | 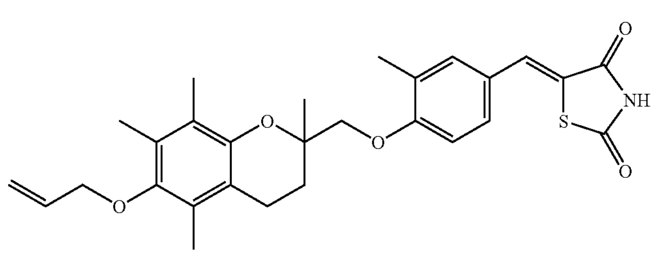 |

TABLE 12-continued

| Entry | compound | structure |
|---|---|---|
| 18 | TG-30 | 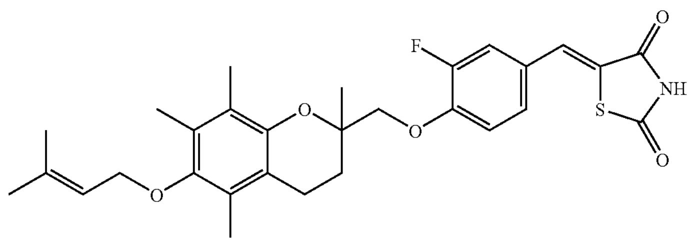 |
| 19 | TG-31 | 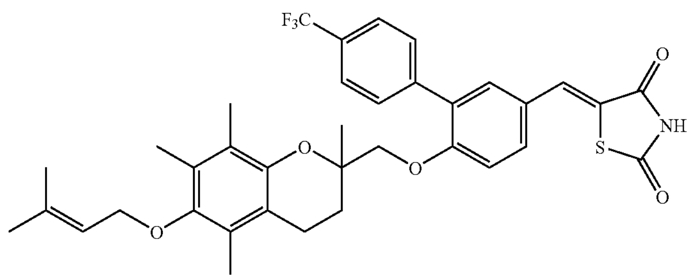 |
| 20 | TG-32 | 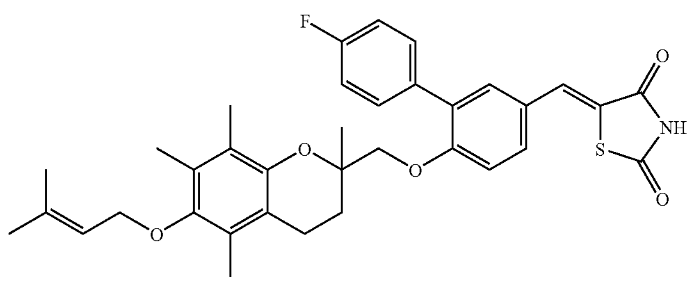 |
| 21 | TG-33 | 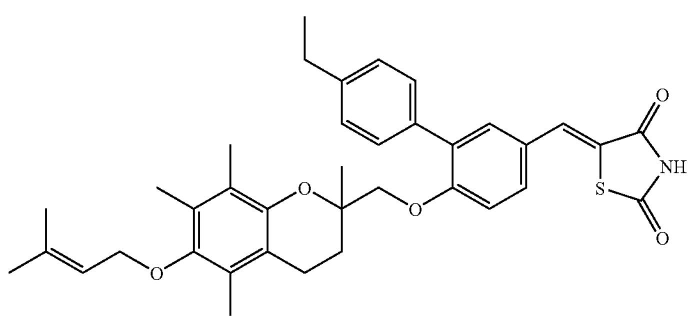 |
| 22 | TG-34 | 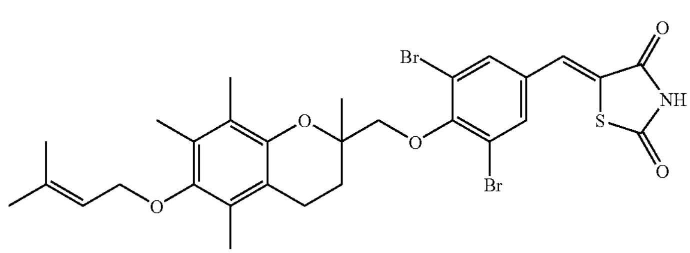 |

TABLE 12-continued
| Entry | compound | structure |
|---|---|---|
| 23 | TG-35 | 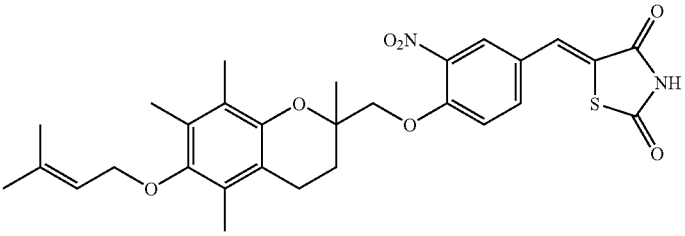 |
| 24 | TG-36 | 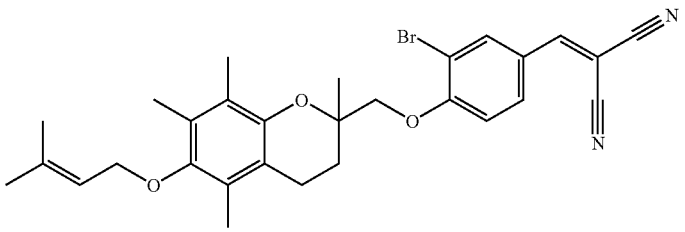 |
| 25 | TG-37 | 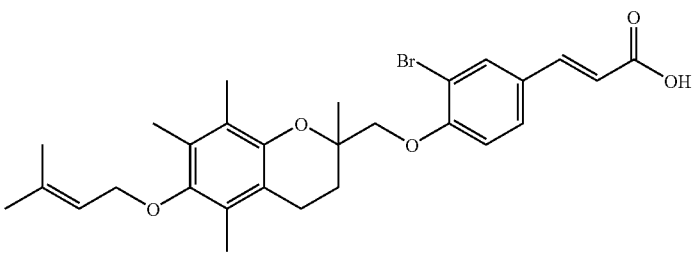 |
| 26 | TG-38 | 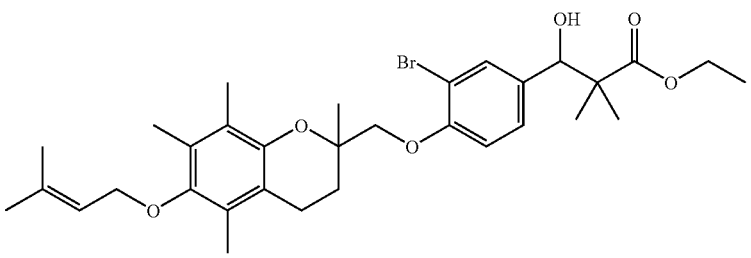 |
| 27 | TG-39 | 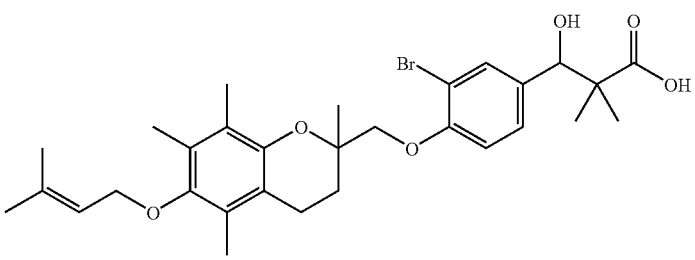 |
| 28 | TG-41 | 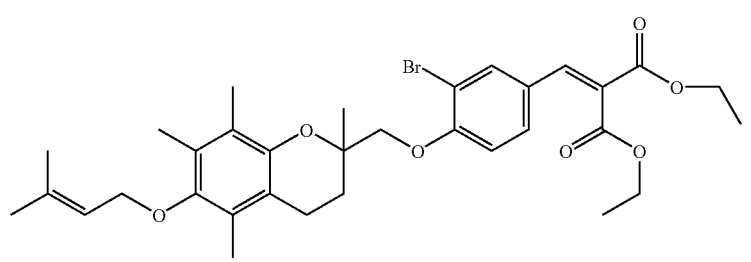 |

TABLE 12-continued
| Entry | compound | structure |
|---|---|---|
| 29 | TG-42 | 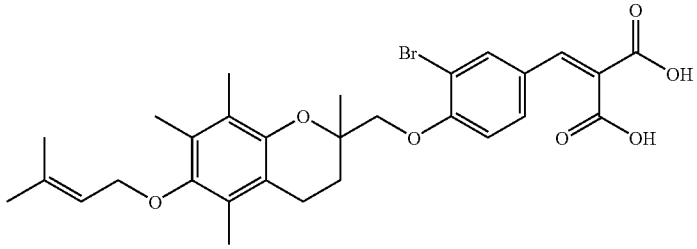 |
| 30 | TG-43 | 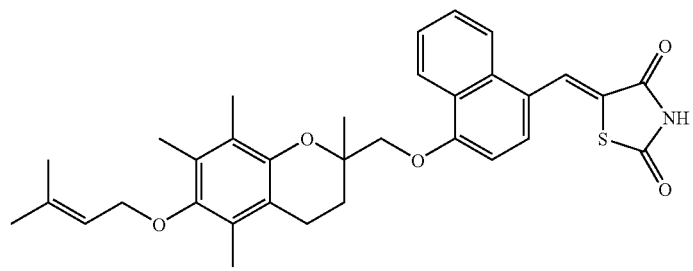 |
| 31 | TG-44 | 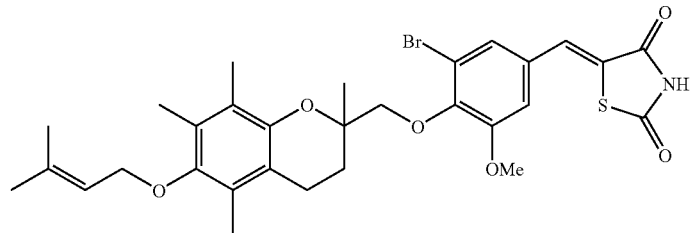 |
| 32 | TG-45 | 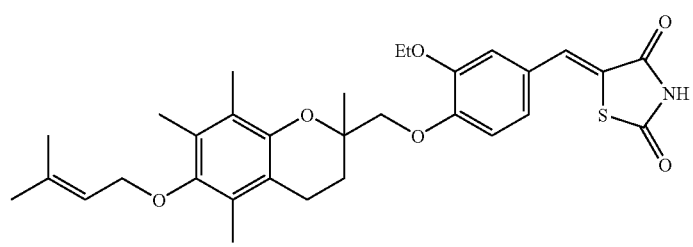 |
| 33 | TG-46 | 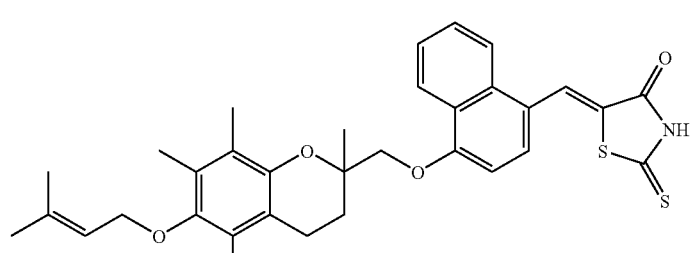 |

TABLE 12-continued
| Entry | compound | structure |
|---|---|---|
| 34 | TG-51 | 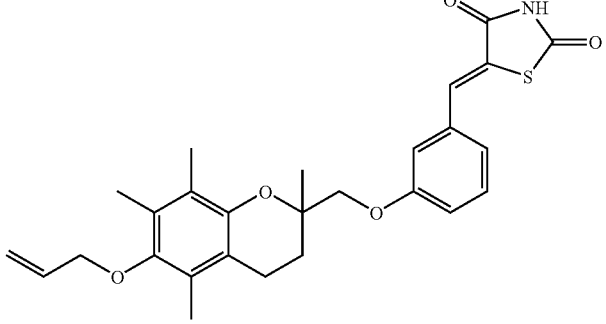 |
| 35 | TG-52 | 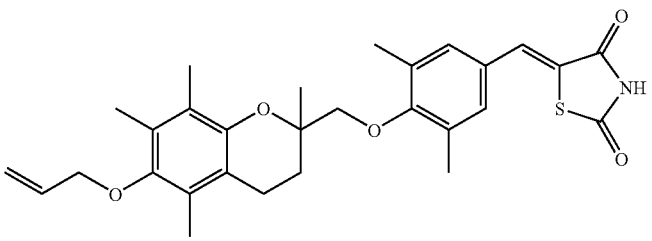 |
| 36 | TG-53 | 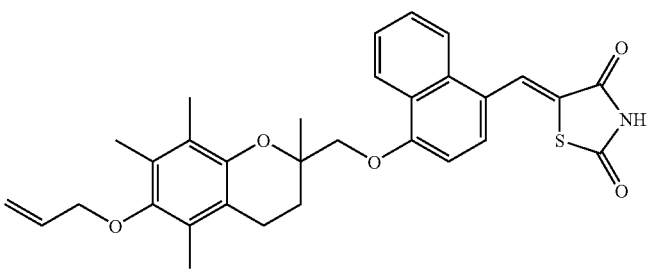 |
| 37 | TG-54 | 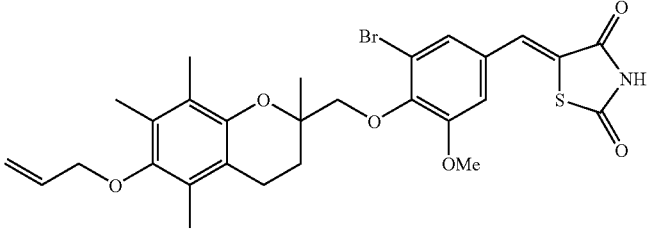 |
| 38 | TG-55 | 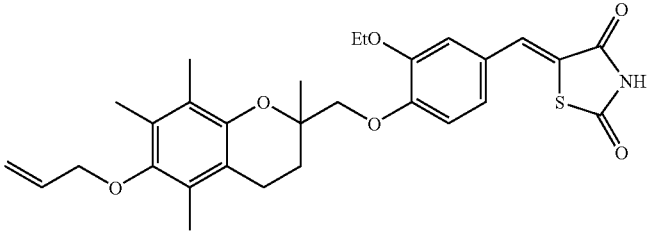 |
| 39 | TG-88 | 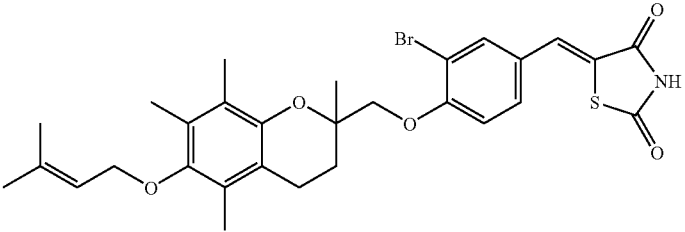 |

TABLE 12-continued

| Entry | compound | structure |
|---|---|---|
| 40 | TG-89 | 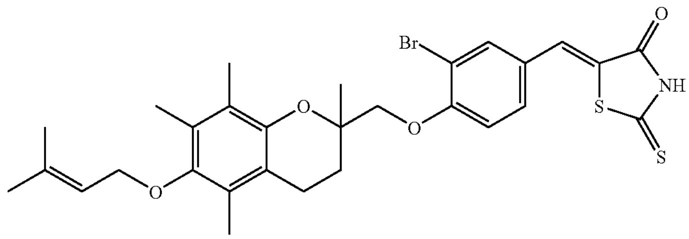 |
| 41 | | 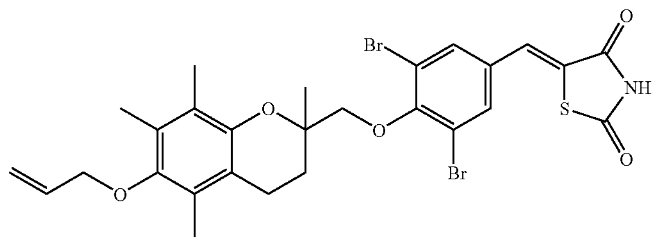 |
| 42 | | 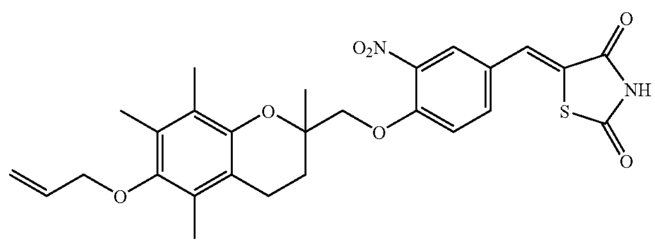 |
| 43 | | 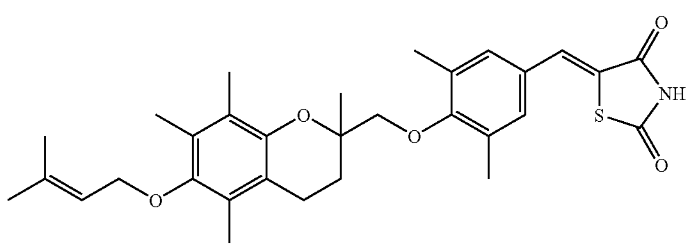 |
| 44 | | 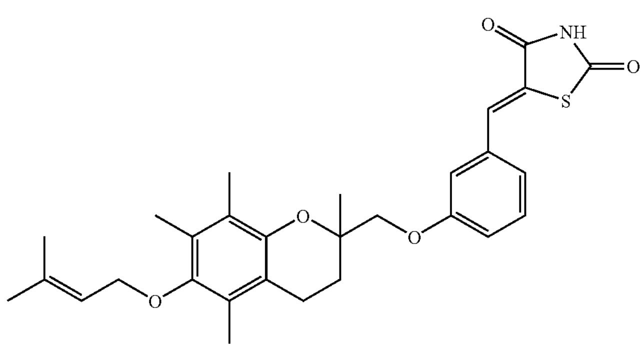 |
| 45 | | 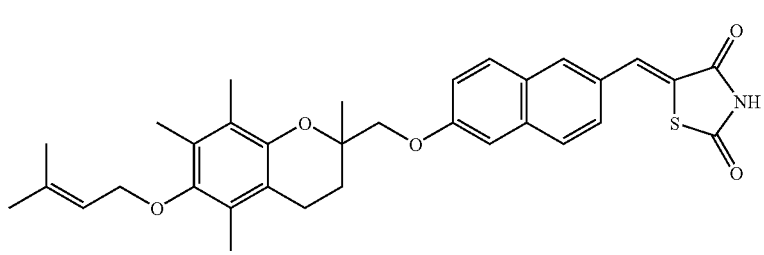 |

TABLE 12-continued

| Entry | compound | structure |
|---|---|---|
| 46 | | 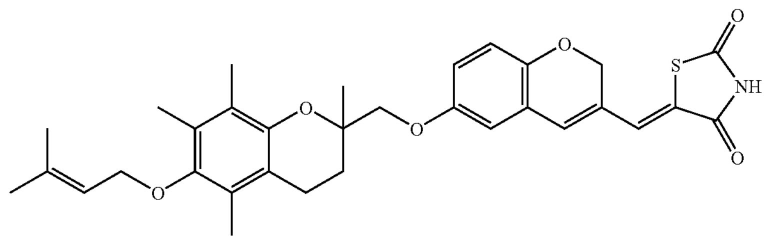 |
| 47 | | 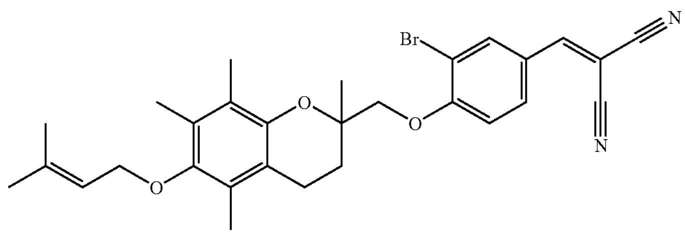 |
| 48 | | 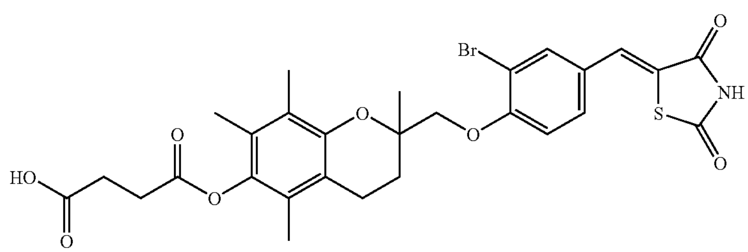 |
| 49 | | 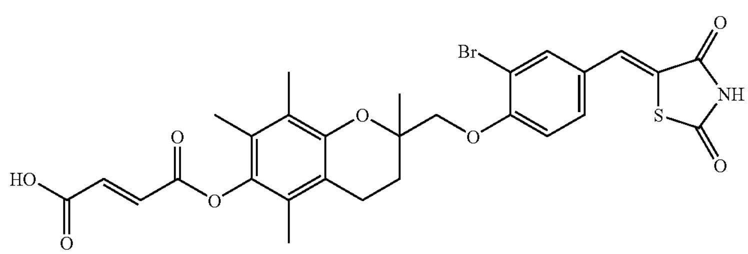 |
| 50 | | 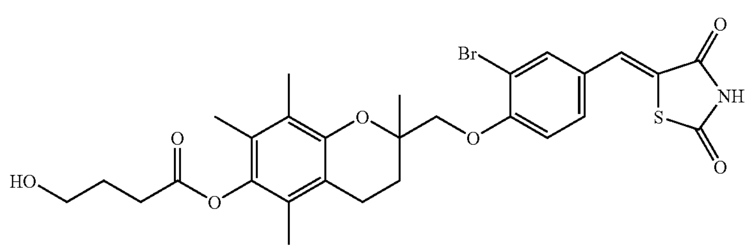 |
| 51 | | 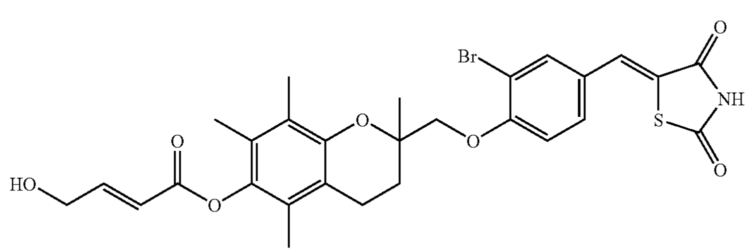 |

TABLE 12-continued
| Entry | compound | structure |
|---|---|---|
| 52 | | 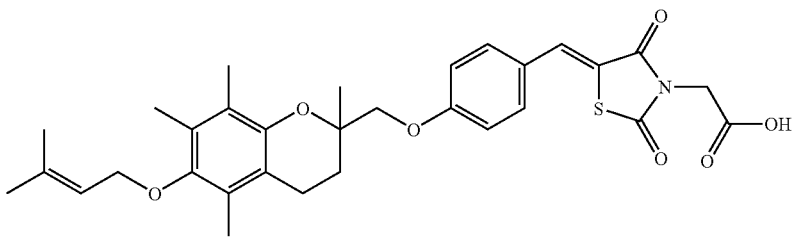 |
| 53 | | 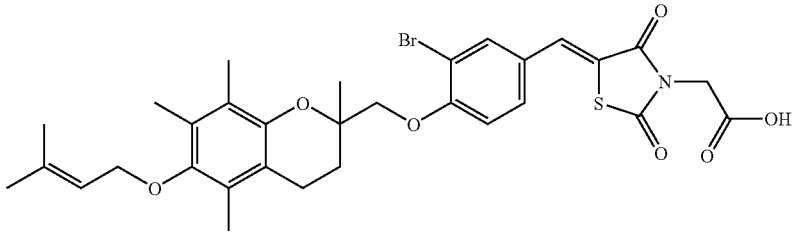 |
| 54 | | 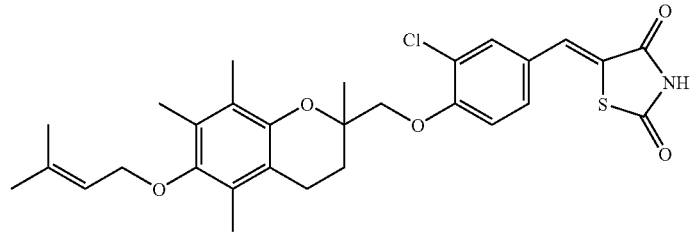 |
| 55 | | 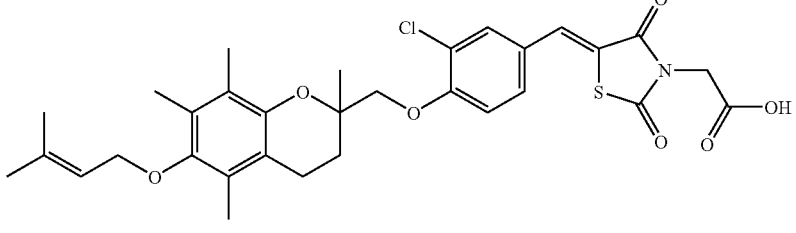 |
| 56 | | 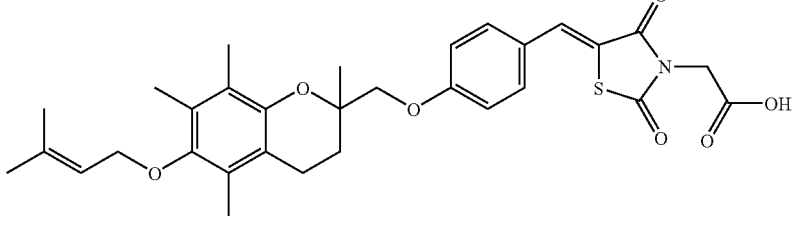 |
| 57 | | 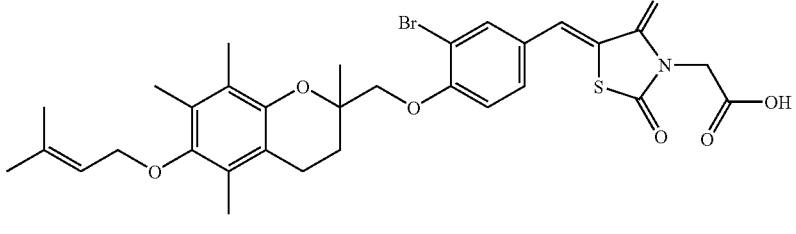 |

TABLE 12-continued
| Entry | compound | structure |
|---|---|---|
| 58 | | 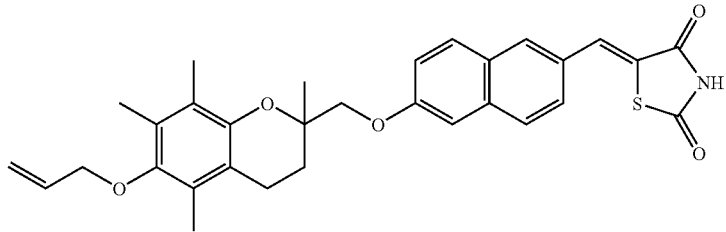 |
| 59 | | 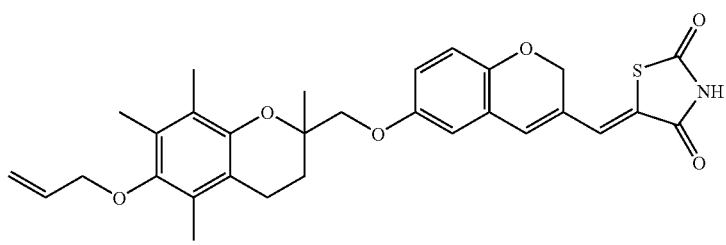 |
| 60 | | 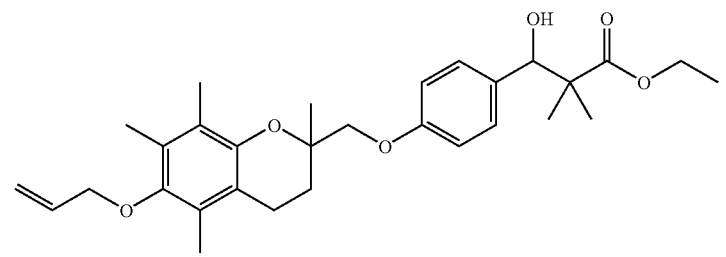 |
| 61 | | 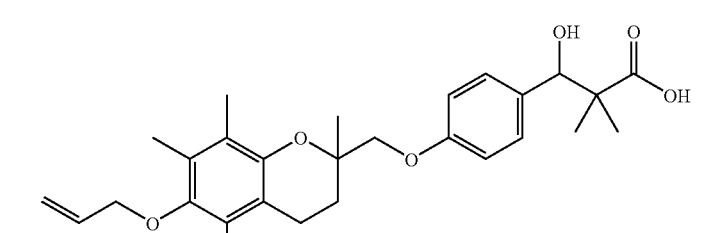 |
| 62 | | 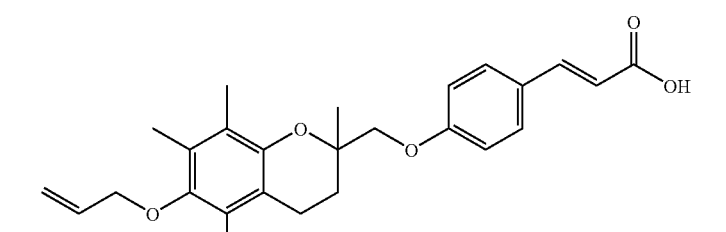 |
| 63 | | 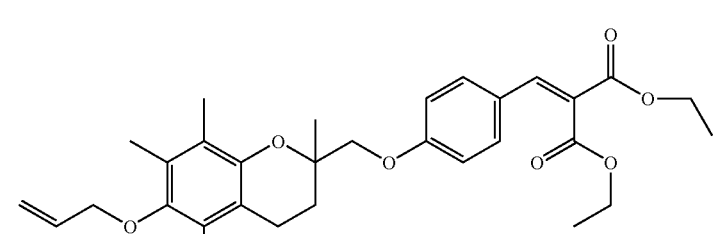 |

TABLE 12-continued
| Entry | compound | structure |
|---|---|---|
| 64 | | 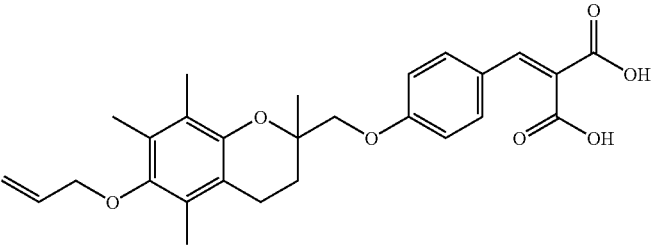 |
| 65 | | 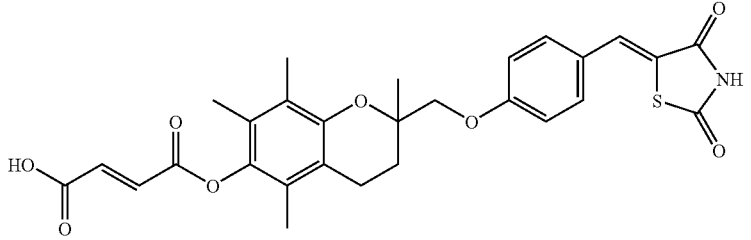 |
| 66 | | 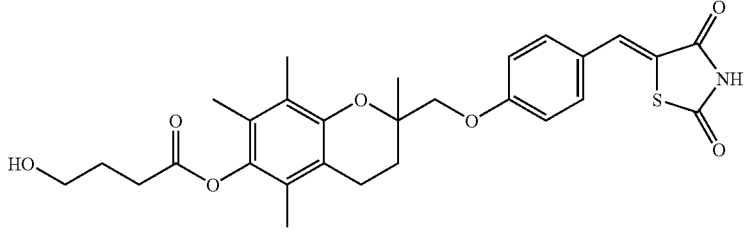 |
| 67 | | 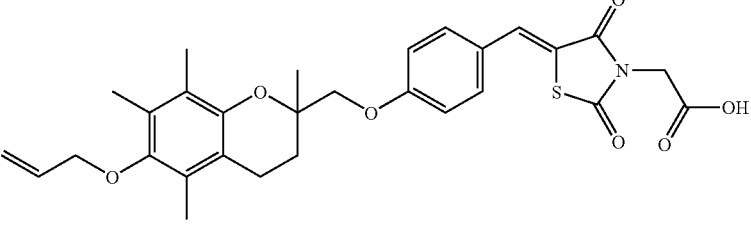 |
| 68 | | 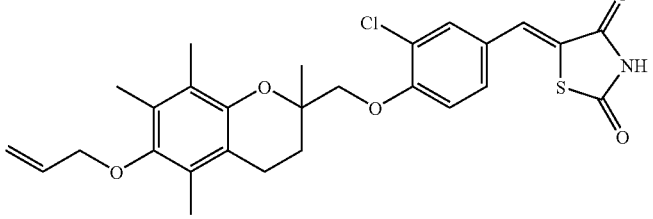 |
| 69 | | 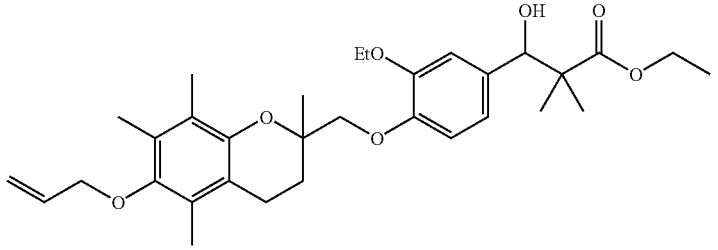 |

TABLE 12-continued
| Entry | compound | structure |
|---|---|---|
| 70 | | 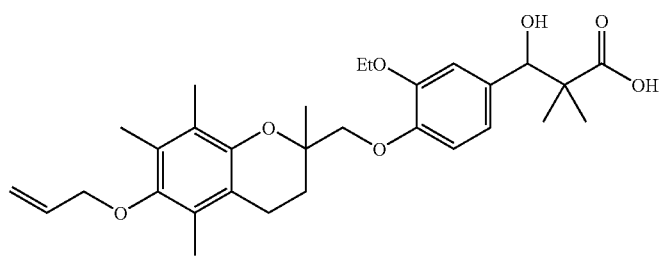 |
| 71 | | 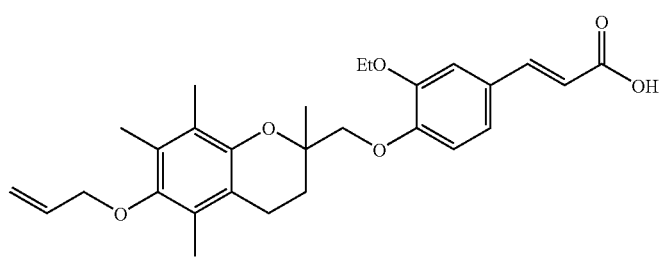 |
| 72 | | 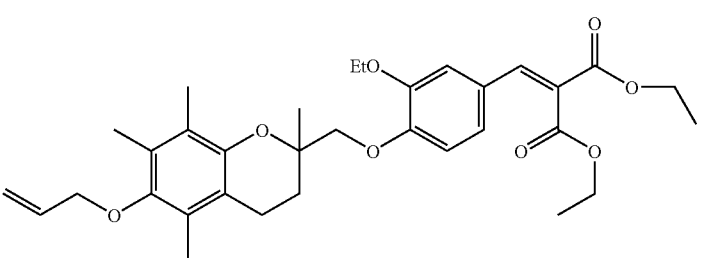 |
| 73 | | 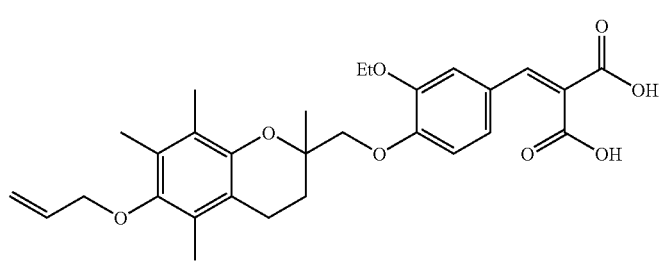 |
| 74 | | 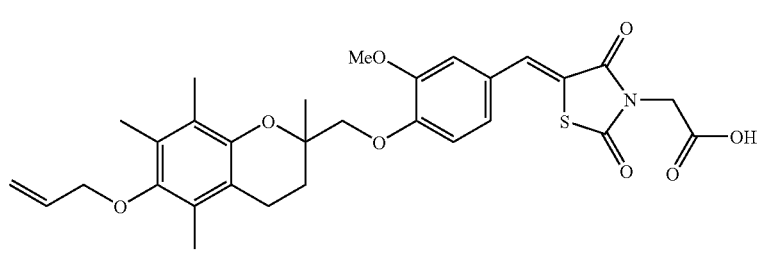 |
| 75 | | 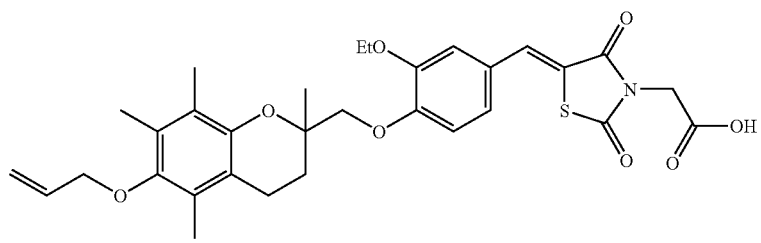 |

TABLE 12-continued

| Entry | compound | structure |
|---|---|---|
| 76 | | 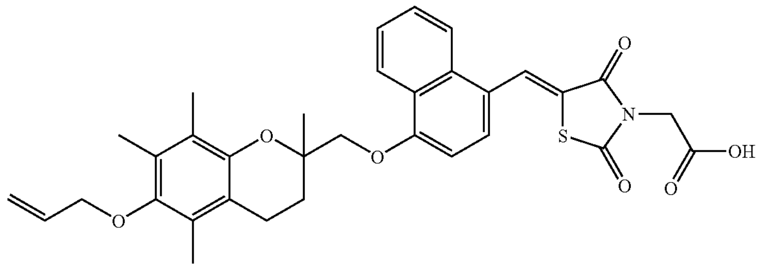 |
| 77 | | 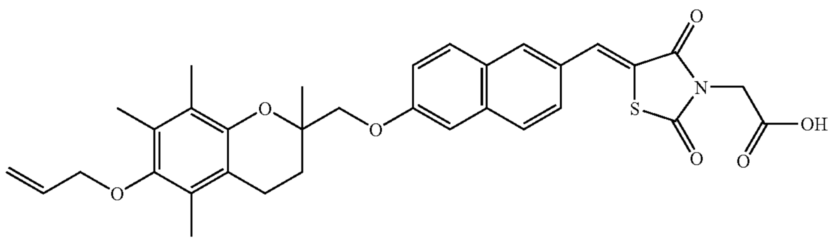 |
| 78 | | 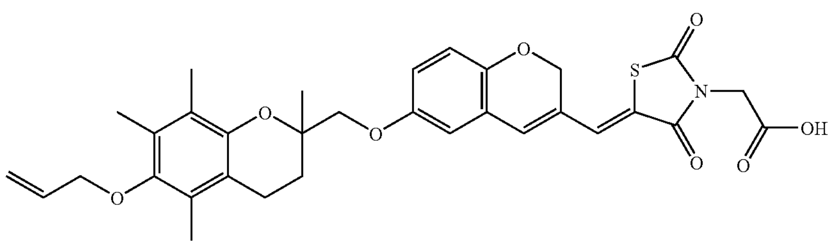 |
| 79 | | 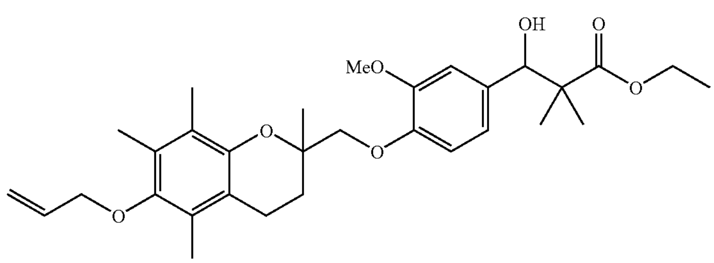 |
| 80 | | 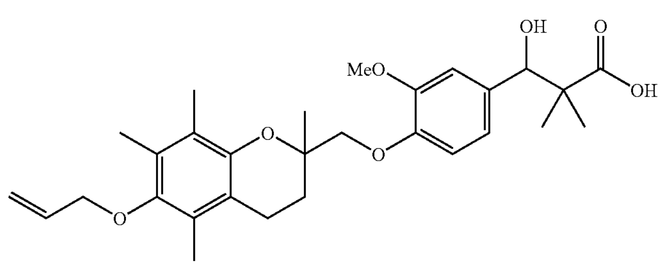 |
| 81 | | 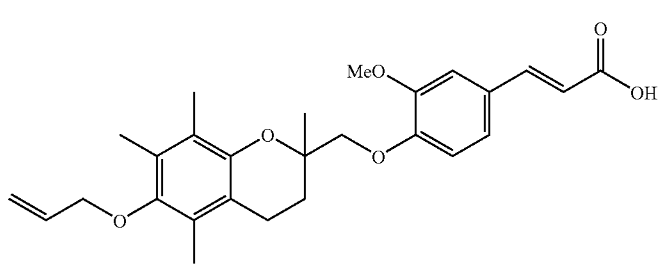 |

TABLE 12-continued

| Entry | compound | structure |
|---|---|---|
| 82 | | *(structure shown)* |
| 83 | | *(structure shown)* |

Materials and Methods

Reagents. Troglitazone (TG), ciglitazone (CG), MG132, lactacystin, and SB216763 were purchased from Sigma (St. Louis, Mo.). Rosiglitazone (RG) and pioglitazone (PG) were prepared from the respective commercial tablets by solvent extraction followed by recrystallization or chromatographic purification. Epoxomicin was a kind gift from Dr. Kyung Bo Kim (University of Kentucky). Δ2-TG {5-[4-(6-hydroxy-2,5,7,8-tetramethyl-chroman-2-ylmethoxy)-benzylidene]-2,4-thiazolidinedione} Δ2-CG {5-[4-(1-methyl-cyclohexyl-methoxy)-benzylidene]-thiazolidine-2,4-dione}, and Δ2-TG-6 {5-[4-(6-allyoxy-2,5,7,8-tetramethyl-chroman-2-ylmethoxy)-benzylidene]-2,4-thiazolidinedione} are TZD derivatives devoid of activity in PPARγ activation, the synthesis of which will be published elsewhere. The identity and purity (>99%) of these synthetic derivatives were verified by proton nuclear magnetic resonance, high-resolution mass spectrometry, and elemental analysis. These agents at various concentrations were dissolved in DMSO, and added to cells in medium with a final DMSO concentration of 0.1%. Rabbit antibodies against p-GSK and mouse anti-cyclin D1 and anti-ubiquitin were purchased from Cell Signaling Technology Inc. (Beverly, Mass.). Rabbit antibodies against ER-α (sc-544), CDK2, CDK4, cyclin A, cyclin B, cyclin D2, cyclin D3, cyclin E, and mouse anti-α-tublin were from Santa Cruz Biotechnology, Inc. (Santa Cruz, Calif.). Mouse monoclonal anti-actin was from ICN Biomedicals Inc (Costa Mesa, Calif.).

Cell culture. ER-positive MCF7 and ER-negative MDA-MB-231 breast cancer cells were obtained from the American Type Culture Collection (Manassas, Va.), and were maintained in DMEM-F12 medium supplemented with 10% fetal bovine serum (FBS) at 37° C. in a humidified incubator containing 5% $CO_2$.

Cell viability analysis. The effect of individual test agents on cell viability was assessed by using the MTT [3-(4,5-dimethylthiazol-2-yl)-2,5-diphenyl-2H-tetrazolium bromide] assay in six replicates. Cells were seeded and incubated in 96-well, flat-bottomed plates in DMEM-F12 media with 10% FBS for 24 h, and were exposed to various concentrations of test agents dissolved in DMSO (final DMSO concentration, 0.1%) in 5% FBS-supplemented DMEM-F12 medium. Controls received DMSO vehicle at a concentration equal to that of drug-treated cells. The medium was removed, replaced by 200 μl of 0.5 mg/ml of MTT in 10% FBS-containing RPMI-1640 medium, and cells were incubated in the $CO_2$ incubator at 37° C. for 2 h. Supernatants were removed from the wells, and the reduced MTT dye was solubilized in 200 μl/well DMSO. Absorbance at 570 nm was determined on a plate reader.

Analysis of PPARγ activation. The analysis was carried out by using a PPARγ transcription factor ELISA kit (Active Motif, Carlsbad, Calif.), in which an oligonucleotide containing the peroxisome proliferator response element (PPRE) was immobilized onto a 96-well plate. PPARs contained in nuclear extracts bind specifically to this oligonucleotide and are detected through an antibody directed against PPARγ. In brief, MCF-7 cells were cultured in RPMI 1640 medium supplemented with 10% FBS, and treated with DMSO vehicle or individual test agents, 10 μM each, for 48 h. Cells were collected, and nuclear extracts were prepared with a Nuclear Extract kit (Active Motif, Carlsbad, Calif.). Nuclear extracts of the same protein concentration from individual treatments were subject to the PPARγ transcription factor ELISA according to the manufacturer's instruction.

Western Blot Analysis. MCF-7 or MDA-MB-231 cells were seeded in 10% FBS-containing DMEM-F-12 for 24 h and treated with various agents as indicated. After individual treatments for 24 h, both the incubation medium and adherent cells in T-25 or T-75 flasks were scraped and collected by centrifugation at 2,000×g for 10 min. The pellets were recovered, placed on ice, and triturated with 20 to 50 μl of a chilled lysis buffer (M-PER® Mammalian Protein Extraction Reagent, Pierce, Rockford, Ill.) to which was added 1% protease inhibitor cocktail (set III, EMD Biosciences, Inc. San Diego, Calif.). After a 30 min-incubation on ice, the mixture was centrifuge at 16,100×g for 3 min. Two μl of the suspension was taken for protein analysis using the Bradford assay kit (Bio-Rad, Hercules, Calif.). To the remaining solution was added the same volume of 2× SDS-PAGE sample loading buffer (100 mM Tris-HCl, pH 6.8, 4% SDS, 5% β-mercaptoethanol 20% glycerol, and 0.1% bromophenol blue). The mixture was boiled for 10 min. Equal amounts of proteins were loaded onto 10% SDS-PAGE gels. After electrophoresis, protein bands were transferred to nitrocellulose membranes in a semi-dry transfer cell. The transblotted membrane was blocking with TBST [Tris-buffered saline (TBS) containing 0.1% Tween 20] containing 5% nonfat milk for 90 min, and the membrane was incubated with the appropriate primary antibody in TBST-5% nonfat milk at 4° C. overnight. After washing three times with TBST for a total of 45 min, the transblotted membrane was incubated with goat anti-rabbit or anti-mouse IgG-horseradish peroxidase conjugates (diluted 1:1000) for 1 h at room temperature and washed four times with TBST for a total of 1 h. The immunoblots were visualized by enhanced chemiluminescence.

Coimmunoprecipitation/Western Blot. MCF-7 cells were cultured in 10% FBS-containing DMEM-F-12 in 75-mm plates for 24 h. Cell were treated with DMSO vehicle, 30 µM TG, or 20 µM Δ2-TG in 5% FBS-containing DMEM-F12 medium for another 20 hours. Cells were rinsed with PBS at room temperature, scraped off the flask, transferred into centrifuge tubes, and centrifuged at 2,000×g for 10 min to pellet the cells. The pellet was resuspended in ice-cold 0.5 ml of RIPA buffer (50 mM Tris-HCl, pH 7.4, 1% NP-40, 0.25% sodium deoxycholate, 150 mM NaCl, 1 mM EDTA, 1% protease inhibitor cocktail), and gently mixed on an orbital shaker at 4° C. for 15 min followed by centrifugation at 14,000×g for 15 min to yield cell lysates. These cell lysates were treated with 100 µl of protein A-agarose bead slurry, followed by brief centrifugation, to remove nonspecific binding proteins. Equal amounts of proteins from these lysates, as determined by the Bradford assay, were mixed with anti-cyclin D1 in an orbital shaker at 23° C. for 2 h, followed by 100 µl of protein A-agarose bead slurry at 4° C. for 12 h. The immunocomplex was collected by brief centrifugation, washed 4 times with 800 µl of ice-cold RIPA buffer, and suspended in 50 µl of the aforementioned 2× SDS sample loading buffer. The suspension was boiled for 10 min, cooled, and briefly centrifuged to remove the beads. Western blot analysis was performed with anti-cyclin D1 or anti-ubiquitin as described above.

Reverse transcriptase (RT-) PCR analysis of mRNA transcripts of cyclin D1 gene. MCF7 cells were subject to total RNA isolation by using RNeasy mini kit (Qiagen, Valencia, Calif.). RNA concentrations and quality were assessed spectrophotometrically by measuring absorption at 260 nm. Aliquots of 20 µg of total RNA from each sample was reverse transcribed to cDNA using Omniscript RT Kit (Qiagen) according to manufacturer's instructions. The primers used were as follows: cyclin D1, forward, 5'-ATGGAACAC-CAGCTCCTGTGCTGC-3', reverse, 5'-TCAGATGTC-CACGTCCCGCACGT-3'; β-actin, forward, 5'-TCTACAAT-GAGCTGCGTGTG-3', reverse, 5'-GGTCAGGATCTTCATGAGGT-3'. The reaction conditions were as follows: for cyclin D1 (a) initial denaturation at 95° C. for 5 min; (b) 34 cycles of amplification (95° C. for 1 min, 65° C. for 1 min 45 s, and 72° C. for 1 min); and (c) a final extension step of 10 min at 72° C.; for β-actin (a) initial denaturation at 95° C. for 3 min; (b) 40 cycles of amplification (95° C. for 30 s, 58° C. for 20 s, and 72° C. for 45 s); and (c) a final extension step of 10 min at 72° C. The PCR reaction products were separated electrophoretically in a 1.2 % agarose gel and stained with ethidium bromide.

Results

Effect of TZDs on cyclin D1 downregulation is independent of PPARγ. Three lines of evidence suggest that TZD-mediated cyclin D1 down-regulation in breast cancer cells was independent of PPARγ activation. First, we assessed the effect of TG on cyclin D1 expression in two breast cancer cell lines: ER-positive MCF-7 and ER-negative MDA-MB-231. Among many genotypic differences, these two cell lines exhibit differential PPARγ expression, i.e., PPARγ expression in MDA-MB-231 cells was at least an-order-of-magnitude higher than that of MCF-7 cells (FIG. 1A). Despite this discrepancy, MCF-7 cells showed a higher degree of susceptibility to TG-mediated cyclin D1 down-regulation as compared to the PPARγ-rich MDA-MB-231 cells (panel B).

Second, we assessed the effect of four different TZDs, i.e., TG, CG, rosiglitazone (RG) and pioglitazone (PG), on intracellular cyclin D1 in MCF-7 cells. Among them, TG and CG at high doses were effective in reducing cyclin D1 and ERα levels (FIGS. 2B and C). In contrast, RG and PG lacked appreciable effects at comparable concentrations (data not shown) even though these two agents are more active than TG and CG in PPARγ activation.

Third, we examined the effect of GW9962, a potent PPARγ antagonist (Leesnitzer et al., 2002; Seargent et al., 2004) on TG-mediated cyclin D1 repression in MCF-7 cells. Even at concentrations three orders of magnitude higher than the IC$_{50}$ in PPARγ binding, GW9962 had no appreciable effect on cyclin D1 expression, and did not prevent TG-mediated cyclin D1 down-regulation.

Separation of the cyclin D1-ablative effect from the PPARγ agonist activity. To further discern the role of PPARγ in TZD-induced cyclin D1 ablation, we synthesized the unsaturated derivatives of TG and CG, i.e., Δ2-TG and Δ2-CG (FIG. 2A), both of which were inactive in PPARγ activation (right panel). The effects of TG, CG, and their Δ2-counterparts on the expression of cyclin D1 and ERα in MCF-7 cells were analyzed by Western blotting. As shown, Δ2-TG and Δ2-CG, though devoid of PPARγ activity, were able to reduce the expression levels of cyclin D1 and ERα in MCF-7 cells in a dose-dependent manner with potency higher than that of TG and CG (FIG. 2B). For example, the minimum concentration required for the complete ablation of cyclin D1 was 30 µM for both Δ2-TG and Δ2-CG, as compared to 40 and 50 µM for TG and CG, respectively. In contrast, the effect of these agents on ERα lagged behind that of cyclin D1, requiring substantially higher concentrations to achieve the same extent of repression.

Figure 3:
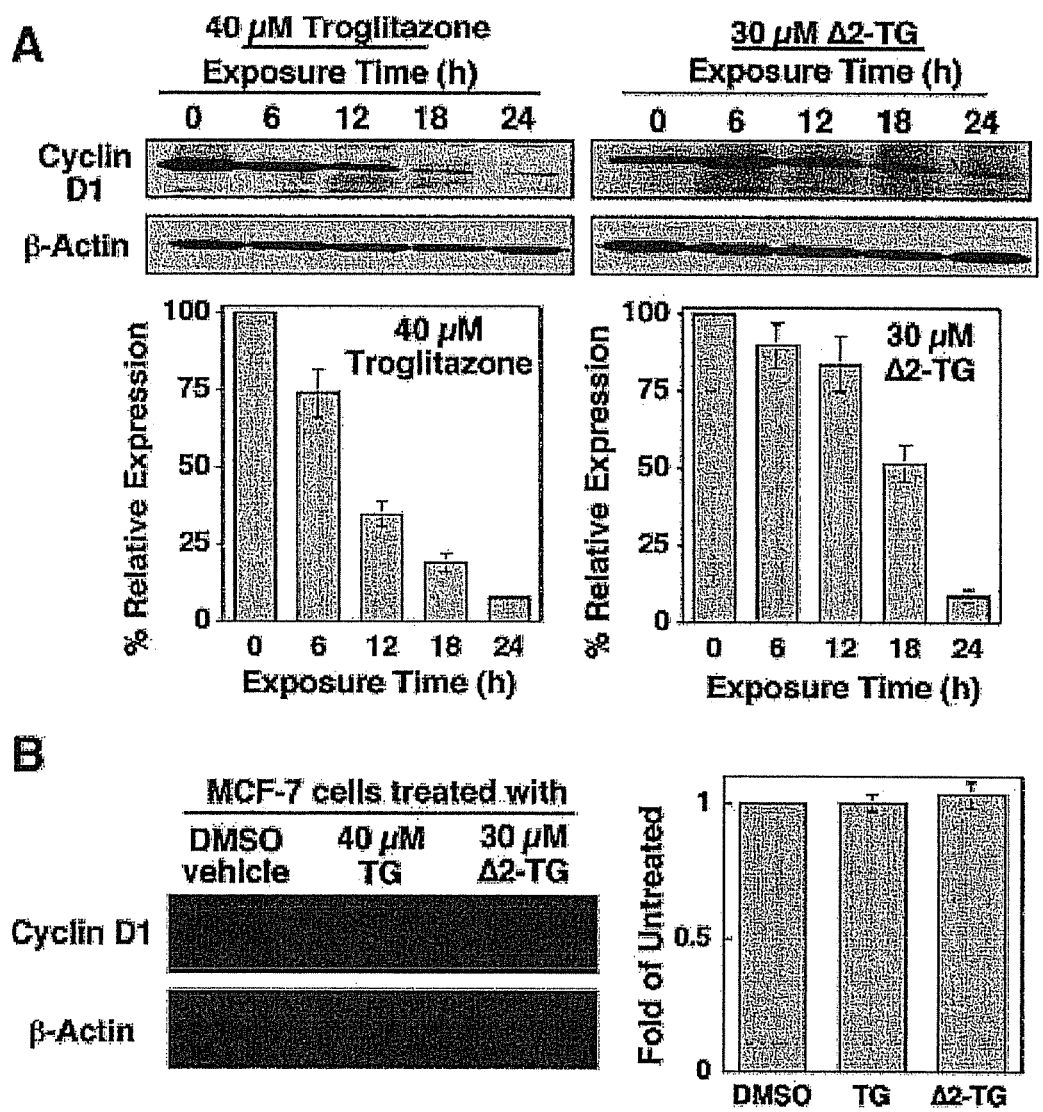
FIG. 3. TG- and Δ2-TG-mediated cyclin D1 ablation is mediated at the post-transcriptional level. A, time-dependent effect of 40 μM TG and 30 μM Δ2-TG on cyclin D1 expression in MCF-7 cells. B, RT-PCR analysis of the mRNA transcripts of cyclin D1 gene in MCF-7 cells after exposure to 40 μM TG or 30 μM Δ2-TG for 24 h. Signals were quantitated by densitometry and normalized against β-actin measurements (lower panel). Each data point represents mean±S.D. (n=3).

FIG. 3A depicts the time course of cyclin D1 down-regulation by 40 µM TG and 30 µM Δ2-TG in MCF-7 cells. Both agents achieved complete ablation at 24 h after treatment. However, semi-quantitative PCR shows that the mRNA level of cyclin D1 remained unaltered after 24 h-exposure (FIG. 3), suggesting that TG- and Δ2-TG-induced cyclin D1 ablation was mediated at the posttranscriptional level.

Figure 4:
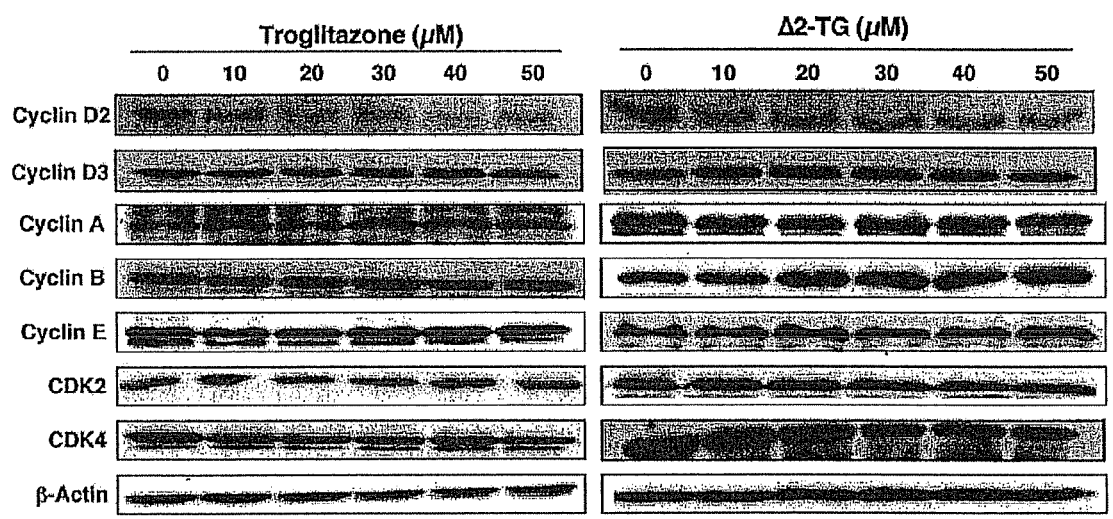
FIG. 4. Dose-dependent effects of TG and Δ2-TG on the expression of cyclins and CDKs. MCF-7 cells were exposed to the individual agents at the indicated concentrations in 5% FBS-supplemented medium for 24 h, and the expression of various cell cycle-regulating proteins was analyzed by Western blot analysis.

To examine whether the ablative effect of TG- and Δ2-TG was unique to cyclin D1, we assessed the expression levels of cyclins D2, D3, A, B, and E, and cyclin-dependent kinases (CDKs) 2 and 4 in MCF cells treated with different doses of TG- and Δ2-TG (FIG. 4). Among these cell cycle-regulating proteins, while cyclin D2 and CDK4 showed a slight decrease in the expression level, no appreciable effect was observed with the other cyclins and CDKs, indicating that the ablative effect was highly specific.

Figure 5:
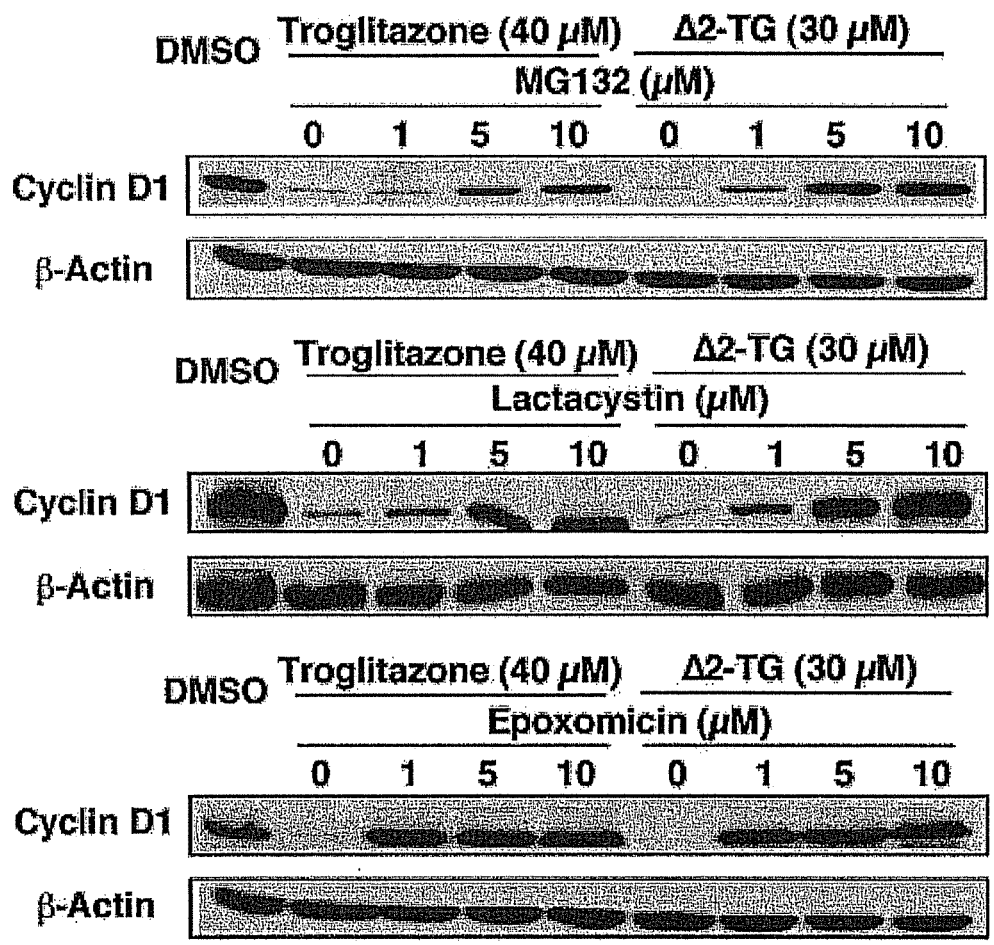
FIG. 5. Dose-dependent effects of the proteasome inhibitors MG132, lactacystin, and epoxomicin on TG- and Δ2-TG-mediated cyclin D1 ablation. MCF-7 cells were exposed to 40 μM TG or 30 μM Δ2-TG in the presence of various concentrations of the proteasome inhibitor in 5% FBS-supplemented medium for 24 h, and the expression of cyclin D1 was analyzed by Western blot analysis.

TG and Δ2-TG facilitate proteasome-mediated proteolysis of cyclin D1. Pursuant to the report that the effect of PGJ$_2$ and CG on cyclin D1 repression was attributable to proteasome-mediated degradation (Choi et al., 1997; Qin et al., 2003), we tested the effect of three proteasome inhibitors (MG132, lactacystin, epoxomicin) on TG and Δ2-TG-facilitated cyclin D1 ablation in MCF-7 cells. As shown in FIG. 5, all three proteasome inhibitors were effective in rescuing the drug-induced cyclin D1 repression.

Figure 6:
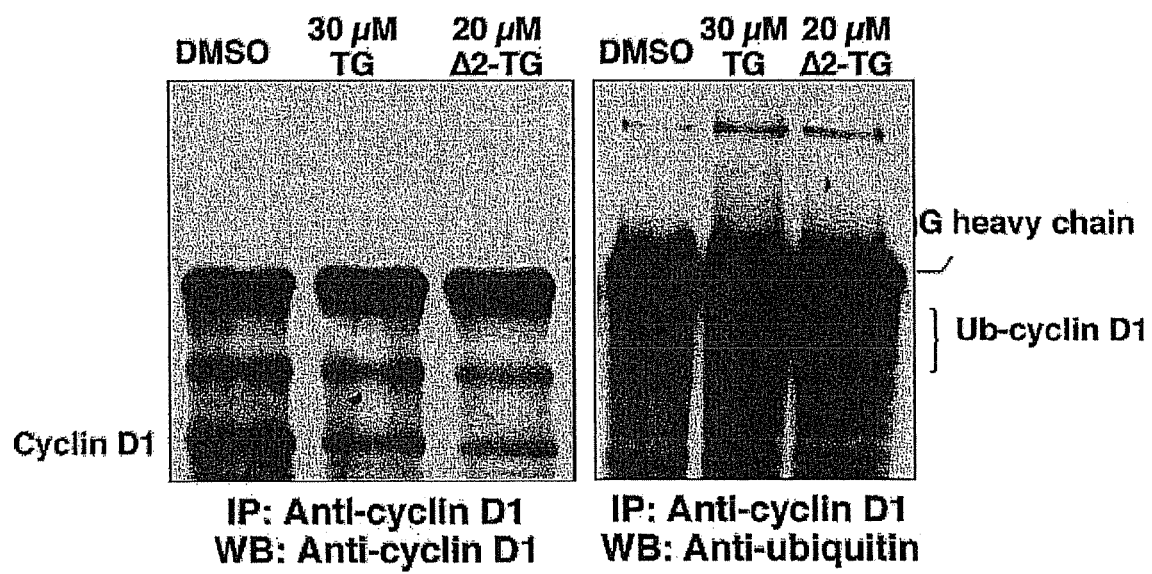
FIG. 6. Cyclin D1 ubiquitination in TG- and Δ2-TG-treated MCF-7 cells. Cell were treated with DMSO vehicle, 30 μM TG, or 20 μM Δ2-TG in 5% FBS-containing medium for 20 h. Cell lysates were immunoprecipitated with anti-cyclin D1, and the immunoprecipitates were analyzed by Western blotting with anti-cyclin D1 or anti-ubiquitin as described in the Materials and Methods.
Figure 7:
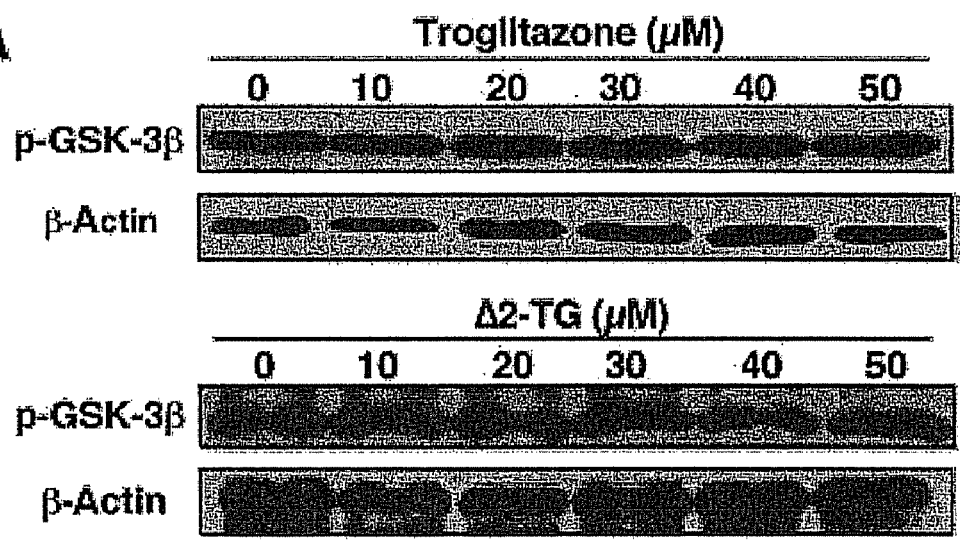
FIG. 7. Evidence that TG and Δ2-TG-induced cyclin D1 down-regulation is independent of GSK-3β activation. A, the phosphorylation levels of GSK-3β remained unaltered in MCF-7 cells treated with different doses of TG and Δ2-TG. B, the GSK-3β inhibitor SB216763 could not rescue TG- and Δ2-TG-induced cyclin D1 ablation.
Figure 7:
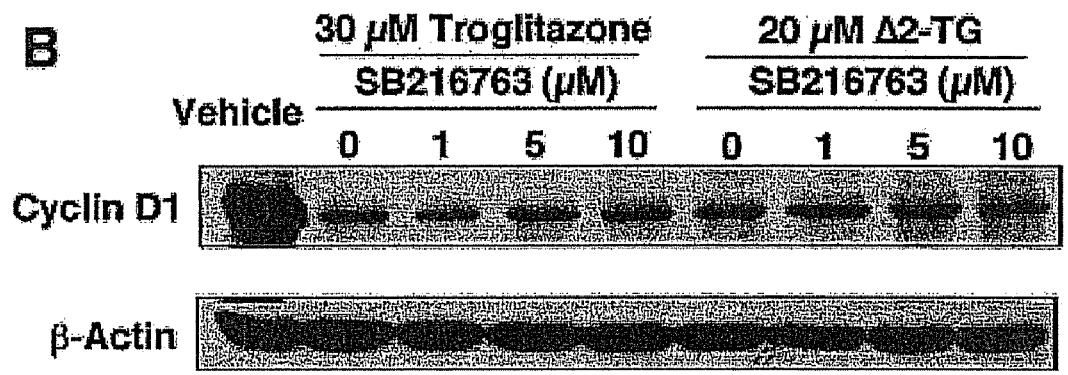

As proteasome-facilitated proteolysis of cyclin D1 is preceded by ubiquitination (Coqueret, 2002), we examined the formation of ubiquitinated cyclin D1 in MCF-7 cells treated with the DMSO vehicle, 30 µM TG or 20 µM Δ2-TG for 20 h. The cell lysates were exposed to cyclin D1 antibodies, followed by protein A-beads. Equivalent amounts of the immunoprecipitated proteins were subject to Western blotting with either cyclin D1 or ubiquitin antibodies (FIG. 6). As shown, while cyclin D1 expression was diminished in TG- and Δ2-TG-treated MCF-7 cells (left panel; IP, anti-cyclin D1; WB, anti-cyclin D1), the extent of ubiquitination of cyclin D1 increased as indicated by a complex ladder of ubiquitinated cyclin D1 bands (right panel; IP, anti-cyclin D1; WB, anti-ubiquitin). Recent evidence indicates that cyclin D1 ubiquitination could be facilitated by either a glycogen synthase kinase (GSK)-3β-dependent or -independent pathway. In the GSK-3β-dependent pathway, CDK-bound cyclin D1 undergoes GSK-3β-mediated phosphorylation, followed by translocation to the cytoplasm where it undergoes proteasomal degradation (Diehl et al., 1998; Diehl et al., 1997). Alternatively, free cyclin D1 can be ubiquitinated independently of GSK-3β, though the exact mechanism remains elusive (Germain et al., 2000). Here, we obtained two lines of evidence to exclude the involvement of GSK-3β in TG- and Δ2-TG-facilitated cyclin D1 degradation. First, the GSK-3β phosphorylation level remained unaltered in TG- and Δ2-TG-treated MCF-7 cells (FIG. 7A). Second, co-treatment with the selective GSK-3β inhibitor SB216763 could not rescue TG- or Δ2-TG-induced cyclin D1 ablation (panel B).

Figure 8:
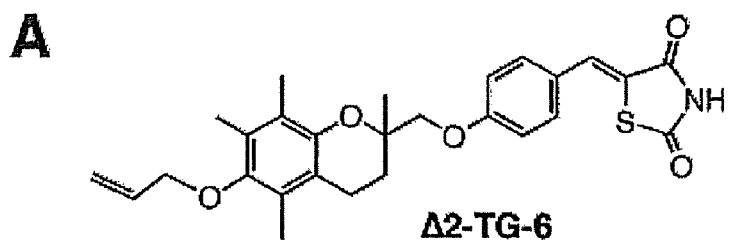
FIG. 8. Δ2-TG-6, a structurally optimized cyclin D1-ablative agent. A, structure of Δ2-TG-6. B, dose-dependent effect of Δ2-TG-6 on cyclin D1 down-regulation in MCF-7 cells. C, Δ2-TG-6-mediated cyclin D1 ablation is facilitated by proteasomal proteolysis. D, dose-dependent effects of Δ2-TG-6 versus TG and Δ2-TG on MCF-7 cell viability. MCF-7 cells were exposed to Δ2-TG-6, TG or Δ2-TG at the indicated concentrations in 5% FBS-supplemented DMEM-F12 medium in 96-well plates for 24 h, and cell viability was assessed by MTT assay. Each data point represents the means of six replicates.
Figure 8:
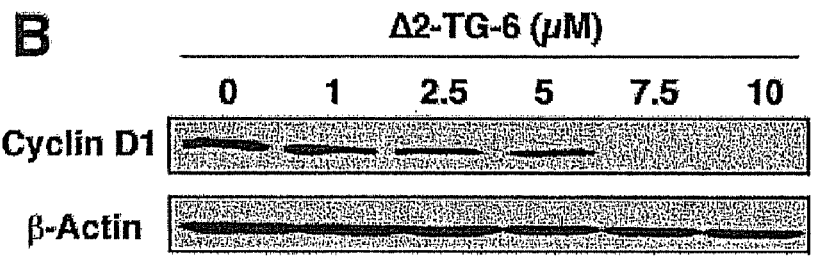
Figure 8:
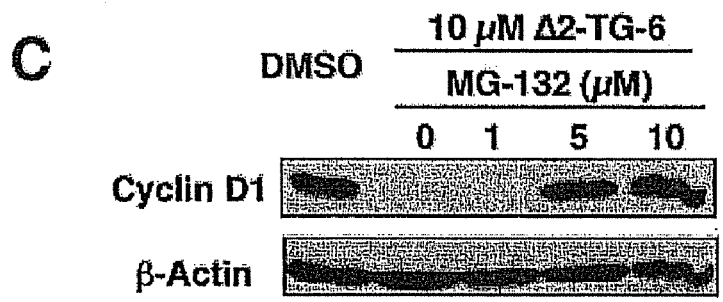
Figure 8:
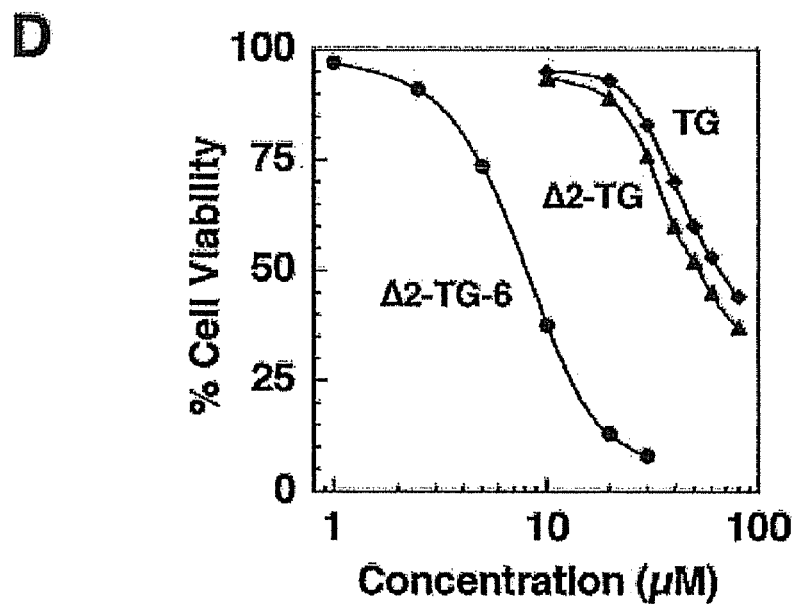

Development of novel Δ2-TG-derived cyclin D1-ablative agents. The findings described above prompted a notion that Δ2-TG could be used as a scaffold to develop novel cyclin D1 ablative agents. Accordingly, a series of Δ2-TG derivatives were synthesized, and their respective activities in ablating cyclin D1 in MCF-7 cells were examined. Among more than 20 derivatives tested, Δ2-TG-6 represented a structurally optimized agent with potency an-order-of-magnitude higher than that of Δ2-TG. Structurally, this increase was attributed to an additional allyl moiety on the terminal hydroxyl function of Δ2-TG (FIG. 8A). As shown, Δ2-TG-6 reduced cyclin D1 levels at concentrations as low as 2.5 µM vis-à-vis ≧20 µM for Δ2-TG (panel B). Like its parent molecule, the effect of Δ2-TG-6 on cyclin D1 ablation could be blocked by the proteasome inhibitor MG-132 (panel C). In line with its enhanced ability in cyclin D1 ablation, Δ2-TG-6 exhibited significantly higher potency than Δ2-TG in inhibiting MCF-7 cell proliferation ($IC_{50}$, 8 µM versus 55 µM) (panel D).

Discussion

A variety of mechanisms have been proposed to account for the ability of various antiproliferative agents to ablate cyclin D1 expression. These include transcriptional repression of the cyclin D1 promoter (flavopiridol and $PGJ_2$) (Carlson et al., 1999; Wang et al., 2001), calpain-mediated proteolytic degradation (lovastatin and actinomycin D) (Choi et al., 1997), and proteasome-facilitated proteolysis (retinoic acid and various PPARγ agonists) (Langenfeld et al., 1997; Lapillonne et al., 2003; Wang et al., 2001)]. From a clinical perspective, this drug-induced cyclin D1 repression not only contributes to the inhibition of breast cancer cell proliferation, but can also overcome drug resistance by sensitizing breast cancer cells to apoptotic signals emanating from Akt inhibition (Wu et al., 2002). Thus, an urgent need exists to develop potent cyclin D1-ablative agents that are effective in the therapeutically attainable range (≦5 µM) for the treatment and/or prevention of breast cancer.

Figure 2:
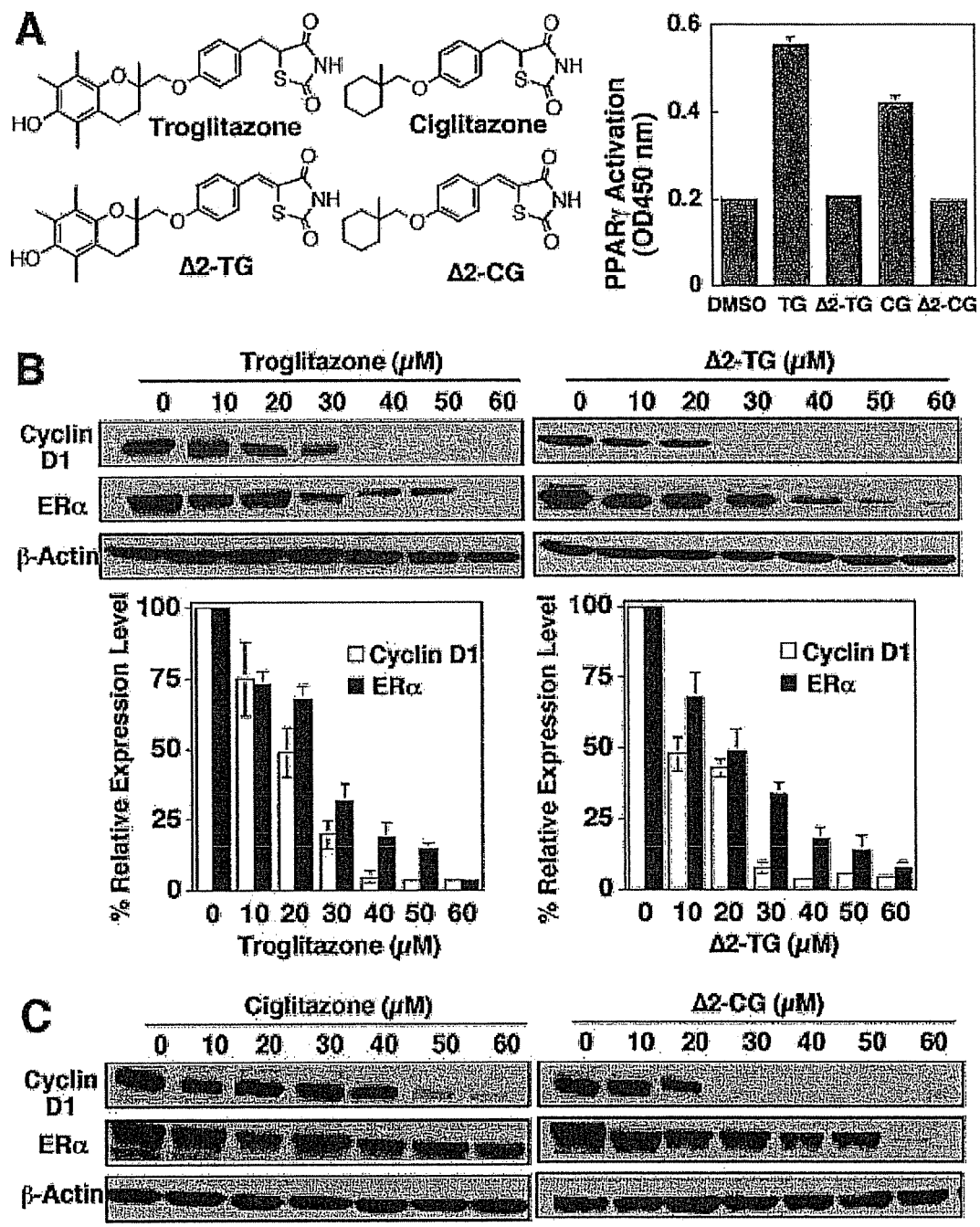
FIG. 2. Pharmacological evidence that the effect of TG and CG on cyclin D1 down-regulation is dissociated from PPARγ activation. A, chemical structures of TG, CG, and the respective Δ2-derivatives and evidence that Δ2-TG and Δ2-CG are devoid of activity in PPARγ activation (right panel). Analysis of PPARγ activation was carried out as described under the Materials and Methods. In brief, MCF-7 cells were exposed to individual test agents (10 μM) or DMSO vehicle in 10% FBS-supplemented RPMI 1640 medium for 48 h. Amounts of PPARγ in the resulting nuclear extracts were analyzed by PPARγ transcript factor ELISA kit. Each data point represents mean+S.D. (n=3). B, dose-dependent effect of TG, Δ2-TG on cyclin D1 and ERα expression in MCF-7 cells. MCF-7 cells were exposed to the individual agents at the indicated concentrations in 5% FBS-supplemented medium for 24 h, and the expression of cyclin D1 and ERα was analyzed by Western blot analysis (upper panel). Signals were quantitated by densitometry and normalized against β-actin measurements (lower panel). Each data point represents mean±S.D. (n=3). C, dose-dependent effect of CG, Δ2-CG on cyclin D1 and ERα expression in MCF-7 cells.

Of the aforementioned agents, the PPARγ agonists TG and CG represent attractive molecules for this drug discovery effort. Thus, we first investigated the mechanism underlying TG- and CG-mediated cyclin D1 down-regulation. Several lines of evidence suggest that the effect of TG and CG on cyclin D1 is independent of PPARγ activation. First, this cyclin D1-ablative effect was not noted with the more potent PPARγ agonists RG and PG at comparable concentrations, and could not be rescued by the PPARγ antagonist GW9662. Second, despite significantly higher PPARγ expression, MDA-MB-231 cells were less susceptible to TG-mediated cyclin D1 ablation. Third, Δ2-TG and Δ2-CG, through devoid of PPARγ activity, were able to mediate cyclin D1 ablation with slightly higher potency than that of TG and CG. Furthermore, TG and Δ2-TG share the mechanism in down-regulating cyclin D1 in MCF-7 cells. Our data indicate that both agents facilitated proteasomal proteolysis via a GSK-3β-independent mechanism. Two lines of evidence suggest that ERα might play a role in the TZD-promoted degradation of cyclin D1. First, the cyclin D1 ablation was accompanied by a decrease in ERα expression in MCF-7 cells (FIG. 2). Second, the ERα-negative MDA-MB-231 cells were more resistant to the cyclin D1-ablative effect of TG (FIG. 1). This TZD-mediated down-regulation of cyclin D1 and ERα is reminiscent of that of the histone deacetylase inhibitor trichostatin A (TSA) (Alao et al., 2004). TSA has been shown to repress cyclin D1 and ERα expression, in part, through the up-regulation of Skp2/p45, a regulatory component of the Skp1/Cullin/F-box complex implicated in the ubiquitination of cyclin D1 (Alao et al., 2004). Involvement of Skp2 in TZD-mediated cyclin D1 ablation is currently under investigation.

The separation of cyclin D1 ablation from PPARγ provides a rationale to use the structure of Δ2-TG as a platform to carry out lead optimization. The proof of principle for this premise was Δ2-TG-6, a close structural analogue that exhibited an-order-of-magnitude higher potency than TG and Δ2-TG in facilitating cyclin D1 repression and inhibiting MCF-7 cell proliferation. The clinical impetus of these small-molecule cyclin D1 ablative agents in breast cancer therapy/prevention is multifold. First, cyclin D1 ablation provides specific protection against breast carcinogenesis (Yu et al., 2001). Second, in light of the role of cyclin D1 overexpression in anti-estrogen resistance, cyclin D1 ablation may help overcome the resistance. Third, the synergistic interaction between flavopiridol and trastuzumab in inhibiting breast cancer cell proliferation was attributable, in part, to the reduction of cyclin D1 expression (Wu et al., 2002). These agents may sensitize cells to the antiproliferative action of either CDK inhibition or Her-2/Akt inhibition. Consequently, structural modifications of Δ2-TG-6 to further enhance its cyclin D1-ablative potency constitute the current focus of this investigation.

Examples described herein are for illustrative purposes only and are not meant to limit the scope of the invention.

REFERENCES

Alao J P, Lam E W, Ali S, Buluwela L, Bordogna W, Lockey P, Varshochi R, Stavropoulou A V, Coombes R C and Vigushin D M (2004) Histone deacetylase inhibitor trichostatin A represses estrogen receptor alpha-dependent transcription and promotes proteasomal degradation of cyclin D1 in human breast carcinoma cell lines. *Clin Cancer Res* 10:8094-104.

Albanese C, Johnson J, Watanabe G, Eklund N, Vu D, Arnold A and Pestell R G (1995) Transforming p21 ras mutants and c-Ets-2 activate the cyclin D1 promoter through distinguishable regions. *J Biol Chem* 270:23589-97.

Bromberg J F, Wrzeszczynska M H, Devgan G, Zhao Y, Pestell R G, Albanese C and Darnell J E, Jr. (1999) Stat3 as an oncogene. *Cell* 98:295-303.

Carlson B, Lahusen T, Singh S, Loaiza-Perez A, Worland P J, Pestell R, Albanese C, Sausville E A and Senderowicz A M (1999) Down-regulation of cyclin D1 by transcriptional repression in MCF-7 human breast carcinoma cells induced by flavopiridol. *Cancer Res* 59:4634-41.

Choi Y H, Lee S J, Nguyen P, Jang J S, Lee J, Wu M L, Takano E, Maki M, Henkart P A and Trepel J B (1997) Regulation of cyclin D1 by calpain protease. *J Biol Chem* 272:28479-84.

Coqueret O (2002) Linking cyclins to transcriptional control. *Gene* 299:35-55.

D'Amico M, Hulit J, Amanatullah D F, Zafonte B T, Albanese C, Bouzahzah B, Fu M, Augenlicht L H, Donehower L A, Takemaru K, Moon R T, Davis R, Lisanti M P, Shtutman M, Zhurinsky J, Ben-Ze'ev A, Troussard A A, Dedhar S and Pestell R G (2000) The integrin-linked kinase regulates the cyclin D1 gene through glycogen synthase kinase 3beta and cAMP-responsive element-binding protein-dependent pathways. *J Biol Chem* 275:32649-57.

Diehl J A, Cheng M, Roussel M F and Sherr C J (1998) Glycogen synthase kinase-3beta regulates cyclin D1 proteolysis and subcellular localization. *Genes Dev* 12:3499-511.

Diehl J A, Zindy F and Sherr C J (1997) Inhibition of cyclin D1 phosphorylation on threonine-286 prevents its rapid degradation via the ubiquitin-proteasome pathway. *Genes Dev* 11:957-72.

Germain D, Russell A, Thompson A and Hendley J (2000) Ubiquitination of free cyclin D1 is independent of phosphorylation on threonine 286. *J Biol Chem* 275:12074-9.

Henry D O, Moskalenko S A, Kaur K J, Fu M, Pestell R G, Camonis J H and White M A (2000) Ral GTPases contribute to regulation of cyclin D1 through activation of NF-kappaB. *Mol Cell Biol* 20:8084-92.

Hui R, Finney G L, Carroll J S, Lee C S, Musgrove E A and Sutherland R L (2002) Constitutive overexpression of cyclin D1 but not cyclin E confers acute resistance to antiestrogens in T-47D breast cancer cells. *Cancer Res* 62:6916-23.

Joyce D, Bouzahzah B, Fu M, Albanese C, D'Amico M, Steer J, Klein J U, Lee R J, Segall J E, Westwick J K, Der C J and Pestell R G (1999) Integration of Rac-dependent regulation of cyclin D1 transcription through a nuclear factor-kappaB-dependent pathway. *J Biol Chem* 274:25245-9.

Kenny F S, Hui R, Musgrove E A, Gee J M, Blamey R W, Nicholson R I, Sutherland R L and Robertson J F (1999) Overexpression of cyclin D1 messenger RNA predicts for poor prognosis in estrogen receptor-positive breast cancer. *Clin Cancer Res* 5:2069-76.

Lamb J, Ladha M H, McMahon C, Sutherland R L and Ewen M E (2000) Regulation of the functional interaction between cyclin D1 and the estrogen receptor. *Mol Cell Biol* 20:8667-75.

Langenfeld J, Kiyokawa H, Sekula D, Boyle J and Dmitrovsky E (1997) Posttranslational regulation of cyclin D1 by retinoic acid: a chemoprevention mechanism. *Proc Natl Acad Sci USA* 94:12070-4.

Lapillonne H, Konopleva M, Tsao T, Gold D, McQueen T, Sutherland R L, Madden T and Andreeff M (2003) Activation of peroxisome proliferator-activated receptor gamma by a novel synthetic triterpenoid 2-cyano-3,12-dioxooleana-1,9-dien-28-oic acid induces growth arrest and apoptosis in breast cancer cells. *Cancer Res* 63:5926-39.

Lee R J, Albanese C, Fu M, D'Amico M, Lin B, Watanabe G, Haines G K, 3rd, Siegel P M, Hung M C, Yarden Y, Horowitz J M, Muller W J and Pestell R G (2000) Cyclin D1 is required for transformation by activated Neu and is induced through an E2F-dependent signaling pathway. *Mol Cell Biol* 20:672-83.

Lee R J, Albanese C, Stenger R J, Watanabe G, Inghirami G, Haines G K, 3rd, Webster M, Muller W J, Brugge J S, Davis R J and Pestell R G (1999) pp60(v-src) induction of cyclin D1 requires collaborative interactions between the extracellular signal-regulated kinase, p38, and Jun kinase pathways. A role for cAMP response element-binding protein and activating transcription factor-2 in pp60(v-src) signaling in breast cancer cells. *J Biol Chem* 274:7341-50.

Leesnitzer L M, Parks D J, Bledsoe R K, Cobb J E, Collins J L, Consler T G, Davis R G, Hull-Ryde E A, Lenhard J M, Patel L, Plunket K D, Shenk J L, Stimmel J B, Therapontos C, Willson T M and Blanchard S G (2002) Functional consequences of cysteine modification in the ligand binding sites of peroxisome proliferator activated receptors by GW9662. *Biochemistry* 41:6640-50.

Lukas J, Bartkova J and Bartek J (1996) Convergence of mitogenic signalling cascades from diverse classes of receptors at the cyclin D-cyclin-dependent kinase-pRb-controlled G1 checkpoint. *Mol Cell Biol* 16:6917-25.

Matsumura I, Kitamura T, Wakao H, Tanaka H, Hashimoto K, Albanese C, Downward J, Pestell R G and Kanakura Y (1999) Transcriptional regulation of the cyclin D1 promoter by STAT5: its involvement in cytokine-dependent growth of hematopoietic cells. *Embo J* 18:1367-77.

McIntosh G G, Anderson J J, Milton I, Steward M, Parr A H, Thomas M D, Henry J A, Angus B, Lennard T W and Horne C H (1995) Determination of the prognostic value of cyclin D1 overexpression in breast cancer. *Oncogene* 11:885-91.

McMahon C, Suthiphongchai T, DiRenzo J and Ewen M E (1999) P/CAF associates with cyclin D1 and potentiates its activation of the estrogen receptor. *Proc Natl Acad Sci USA* 96:5382-7.

Musgrove E A, Hunter L J, Lee C S, Swarbrick A, Hui R and Sutherland R L (2001) Cyclin D1 overexpression induces progestin resistance in T-47D breast cancer cells despite p27(Kip1) association with cyclin E-Cdk2. *J Biol Chem* 276:47675-83.

Neuman E, Ladha M H, Lin N, Upton T M, Miller S J, DiRenzo J, Pestell R G, Hinds P W, Dowdy S F, Brown M and Ewen M E (1997) Cyclin D1 stimulation of estrogen receptor transcriptional activity independent of cdk4. *Mol Cell Biol* 17:5338-47.

Prall O W, Rogan E M, Musgrove E A, Watts C K and Sutherland R L (1998) c-Myc or cyclin D1 mimics estrogen effects on cyclin E-Cdk2 activation and cell cycle reentry. *Mol Cell Biol* 18:4499-508.

Qin C, Burghardt R, Smith R, Wormke M, Stewart J and Safe S (2003) Peroxisome proliferator-activated receptor gamma agonists induce proteasome-dependent degradation of cyclin D1 and estrogen receptor alpha in MCF-7 breast cancer cells. *Cancer Res* 63:958-64.

Qin C, Morrow D, Stewart J, Spencer K, Porter W, Smith R, 3rd, Phillips T, Abdelrahim M, Samudio I and Safe S (2004) A new class of peroxisome proliferator-activated receptor gamma (PPARgamma) agonists that inhibit growth of breast cancer cells: 1,1-Bis(3'-indolyl)-1-(p-substituted phenyl)methanes. *Mol Cancer Ther* 3:247-60.

Seargent J M, Yates E A and Gill J H (2004) GW9662, a potent antagonist of PPAR {gamma}, inhibits growth of breast tumour cells and promotes the anticancer effects of the PPAR {gamma} agonist rosiglitazone, independently of PPAR {gamma} activation. *Br J Pharmacol* 143:933-937.

Shtutman M, Zhurinsky J, Simcha I, Albanese C, D'Amico M, Pestell R and Ben-Ze'ev A (1999) The cyclin D1 gene is a target of the beta-catenin/LEF-1 pathway. *Proc Natl Acad Sci USA* 96:5522-7.

Stendahl M, Kronblad A, Ryden L, Emdin S, Bengtsson N O and Landberg G (2004) Cyclin D1 overexpression is a negative predictive factor for tamoxifen response in postmenopausal breast cancer patients. *Br J Cancer* 90:1942-8.

Wang C, Fu M, D'Amico M, Albanese C, Zhou J N, Brownlee M, Lisanti M P, Chatterjee V K, Lazar M A and Pestell R G (2001) Inhibition of cellular proliferation through IkappaB kinase-independent and peroxisome proliferator-activated receptor gamma-dependent repression of cyclin D1. *Mol Cell Biol* 21:3057-70.

Westwick J K, Lambert Q T, Clark G J, Symons M, Van Aelst L, Pestell R G and Der C J (1997) Rac regulation of transformation, gene expression, and actin organization by multiple, PAK-independent pathways. *Mol Cell Biol* 17:1324-35.

Wilcken N R, Prall O W, Musgrove E A and Sutherland R L (1997) Inducible overexpression of cyclin D1 in breast cancer cells reverses the growth-inhibitory effects of anti-estrogens. *Clin Cancer Res* 3:849-54.

Wu K, Wang C, D'Amico M, Lee R J, Albanese C, Pestell R G and Mani S (2002) Flavopiridol and trastuzumab synergistically inhibit proliferation of breast cancer cells: association with selective cooperative inhibition of cyclin D1-dependent kinase and Akt signaling pathways. *Mol Cancer Ther* 1:695-706.

Yin F, Wakino S, Liu Z, Kim S, Hsueh W A, Collins A R, Van Herle A J and Law R E (2001) Troglitazone inhibits growth of MCF-7 breast carcinoma cells by targeting G1 cell cycle regulators. *Biochem Biophys Res Commun* 286:916-22.

Yu Q, Geng Y and Sicinski P (2001) Specific protection against breast cancers by cyclin D1 ablation. *Nature* 411: 1017-21.

Zwijsen R M, Wientjens E, Klompmaker R, van der Sman J, Bernards R and Michalides R J (1997) CDK-independent activation of estrogen receptor by cyclin D1. *Cell* 88:405-15.

The invention claimed is:

1. A compound of formula I:

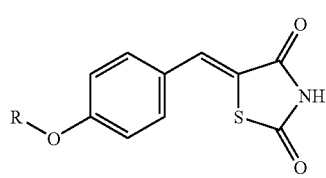

I wherein R is selected from the group consisting of aryl, heteroaryl, cycloalkyl, heterocycloalkyl, alkylaryl, and combinations thereof;

and wherein R may be substituted at one or more substitutable positions with a substituent selected from the group consisting of hydroxyl, alkyl, and combinations thereof with the proviso that R cannot be phenyl.

2. The compound of claim 1, wherein R is selected from the group consisting of

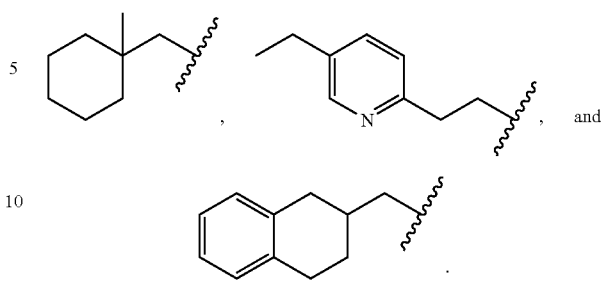

3. A compound of formula II:

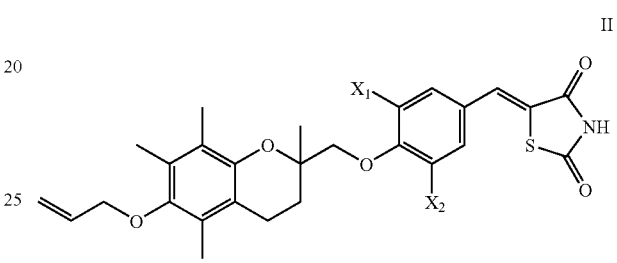

II wherein $X_1$ is selected from the group consisting of H, alkyl, alkoxy, halo, nitro, and combinations thereof; and $X_2$ is selected from the group consisting of H, alkyl, alkoxy, halo, and combinations thereof;

and derivatives and metabolites thereof.

4. The compound of claim 3 wherein $X_1$ is selected from the group consisting of H, Br, $CH_3$, $OCH_3$, $OCH_2CH_3$, $NO_2$, and Cl.

5. The compound of claim 3 wherein $X_2$ is selected from the group consisting of H, $CH_3$, $OCH_3$, and Br.

6. A compound of formula III:

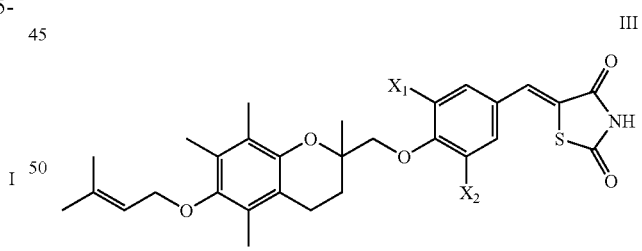

III wherein $X_1$ is selected from the group consisting of H, alkyl, alkoxy, halo, nitro, haloalkylaryl, haloaryl, alkylaryl, and combinations thereof; and $X_2$ is selected from the group consisting of H, alkyl, alkoxy, halo, and combinations thereof.

7. The compound of claim 6 wherein $X_1$ is selected from the group consisting of H, methyl, methoxy, ethoxy, fluoro, chloro, bromo, nitro, trifluoromethylphenyl, fluorophenyl, and ethylphenyl.

8. The compound of claim 6 wherein $X_2$ is selected from the group consisting of H, methyl, methoxy, and bromo.

9. A compound of formula IV:

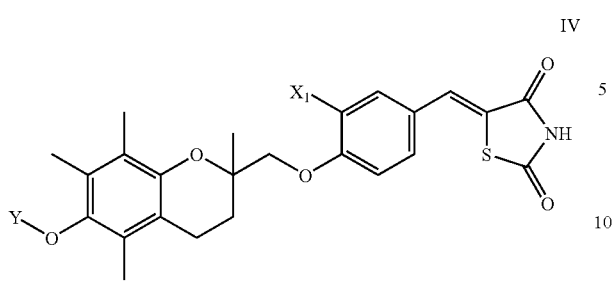

wherein $X_1$ is selected from the group consisting of H and halo; and
Y is selected from the group consisting of alkylaryl, alkenylaryl, alkenyl, ester carboxylic acids, ester alcohols, and combinations thereof.

10. The compound of claim 9 wherein $X_1$ is selected from the group consisting of H and Br.

11. The compound of claim 9 wherein Y is selected from the group consisting of

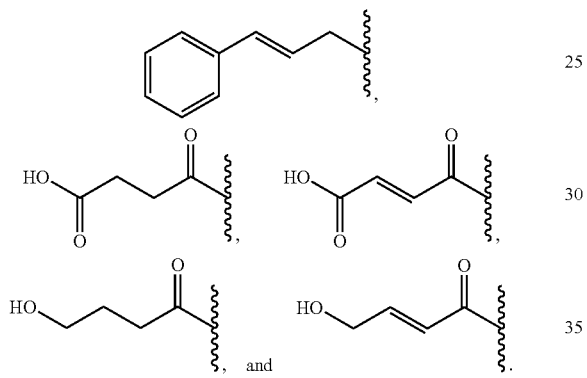

12. A compound of formula V:

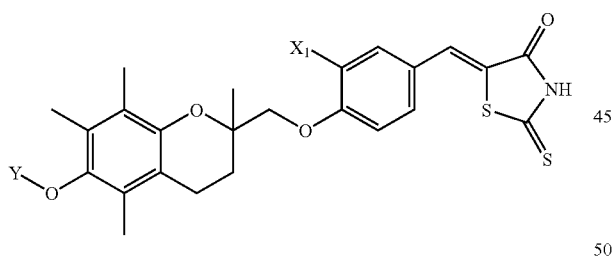

wherein $X_1$ is selected from the group consisting of H and halo; and
Y is selected from the group consisting of straight-chain alkenyl, branched alkenyl, and combinations thereof.

13. A compound of formula VI:

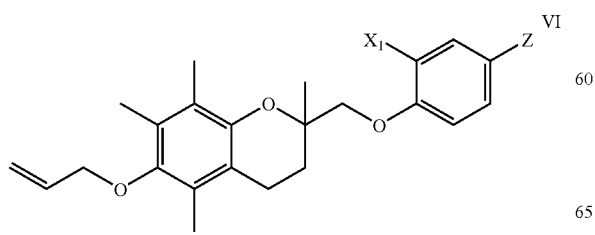

wherein $X_1$ is selected from the group consisting of H, alkoxy, halo, and combinations thereof; and
Z is selected from the group consisting of

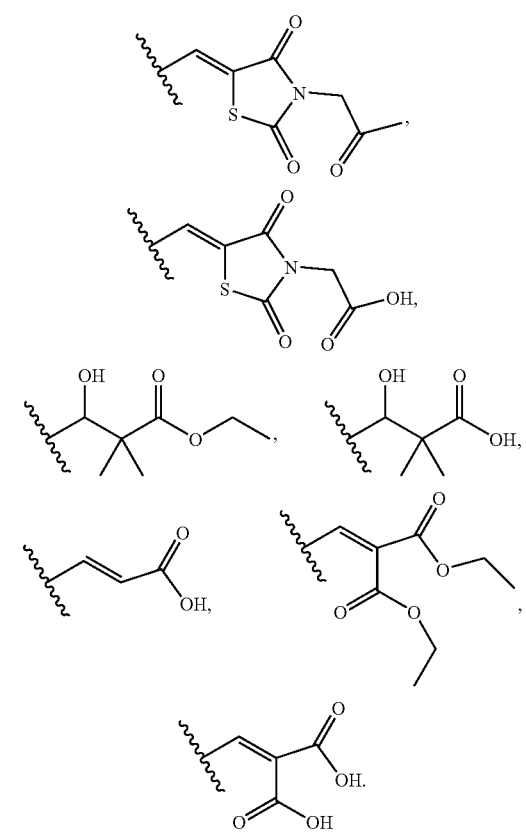

14. A compound of formula VII:

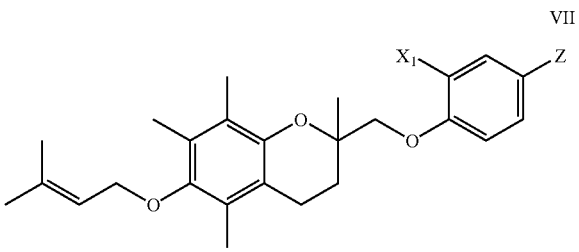

wherein $X_1$ is selected from the group consisting of H and halo; and
Z is selected from the group consisting of

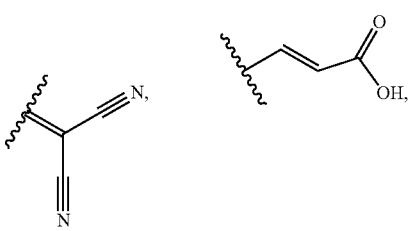

-continued

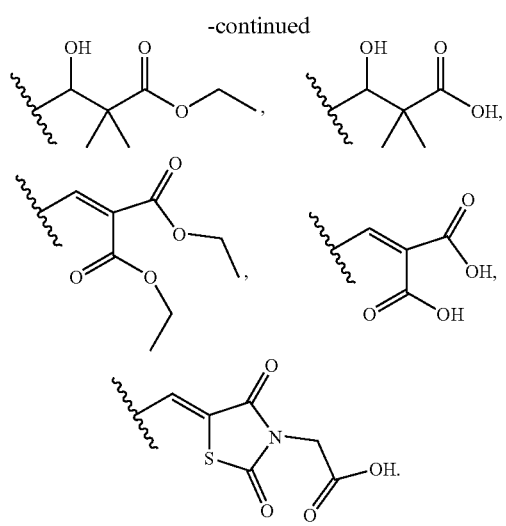

15. A compound of formula VIII:

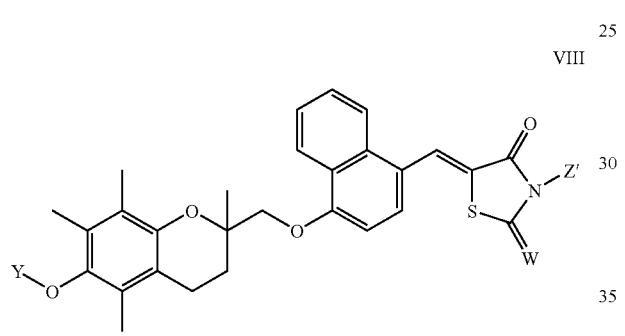

wherein W is selected from the group consisting of O and S;

Y is selected from the group consisting of straight chain alkenyl, branched alkenyl and combinations thereof, and Z' is selected from the group consisting of H and carboxylic acid.

16. A compound of formula IX:

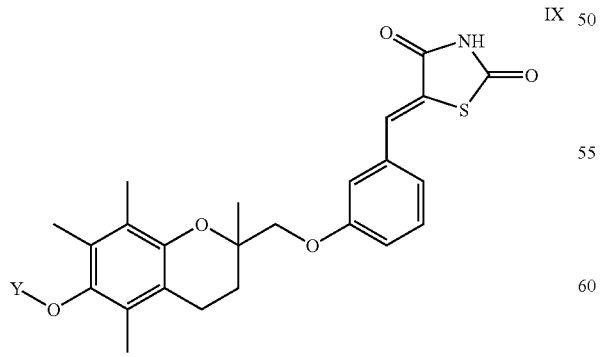

wherein Y is selected from the group consisting of straight chain alkenyl, branched alkenyl and combinations thereof.

17. A compound of formula X:

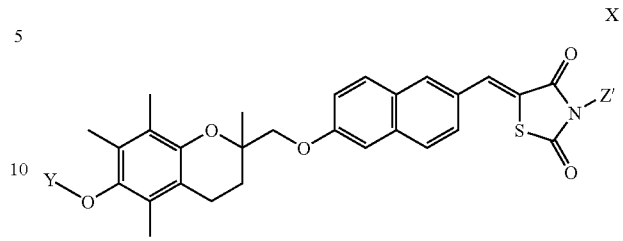

wherein Y is selected from the group consisting of straight chain alkenyl, branched alkenyl and combinations thereof; and Z' is selected from the group consisting of H and carboxylic acid.

18. A compound of formula XI:

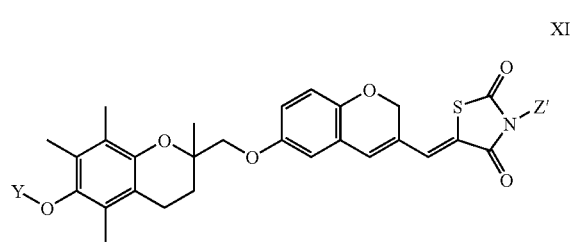

wherein Y is selected from the group consisting of straight chain alkenyl, branched alkenyl and combinations thereof, and Z' is selected from the group consisting of H and carboxylic acid.

19. A compound of formula XII:

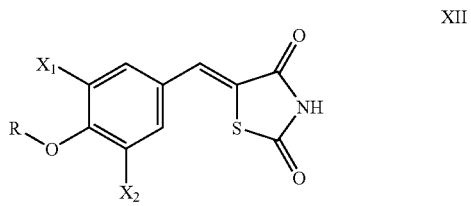

wherein $X_1$ is selected from the group consisting of H, alkyl, alkoxy, halo, haloalkylaryl, haloaryl, alkylaryl, nitro, and combinations thereof; and $X_2$ is selected from the group consisting of H, alkyl, alkoxy, halo, and combinations thereof and wherein R is selected from the group consisting of aryl, heteroaryl, cycloalkyl, heterocycloalkyl, alkylaryl, and combinations thereof; and wherein R may be substituted at one or more substitutable positions with a substituent selected from the group consisting of hydroxyl, alkyl, alkylaryl, alkenyl, alkenylaryl, straight-chain alkenyl, branched alkenyl, alkoxy, alkenoxy, aryloxy, ester carboxylic acids, ester alcohols, and combinations thereof with the proviso that R cannot be phenyl.

20. The compound of claim 1, wherein R is selected from the group consisting of aryl, heteroaryl, cycloalkyl, alkylaryl, and combinations thereof with the proviso that R cannot be phenyl.

21. The compound of claim 19, wherein R is selected from the group consisting of aryl, heteroaryl, cycloalkyl, alkylaryl, and combinations thereof with the proviso that R cannot be phenyl.

* * * * *